(12) United States Patent
Raymond et al.

(10) Patent No.: US 6,440,069 B1
(45) Date of Patent: Aug. 27, 2002

(54) HEALTH MONITORING SYSTEM

(75) Inventors: Stephen A. Raymond, Charlestown; Geoffrey E. Gordon, Boston; Daniel B. Singer, Weymouth, all of MA (US)

(73) Assignee: Brigham & Women's Hospital, Boston, MA (US)

( * ) Notice: Subject to any disclaimer, the term of this patent is extended or adjusted under 35 U.S.C. 154(b) by 0 days.

(21) Appl. No.: 09/940,128

(22) Filed: Aug. 27, 2001

Related U.S. Application Data

(62) Division of application No. 09/447,986, filed on Nov. 23, 1999, now Pat. No. 6,282,441, which is a continuation of application No. 09/001,032, filed on Dec. 30, 1997, now Pat. No. 6,095,985, which is a continuation of application No. 08/394,157, filed on Feb. 24, 1995, now Pat. No. 5,778,882.

(51) Int. Cl.⁷ .................................................. A61B 5/00
(52) U.S. Cl. ........................................................ 600/300
(58) Field of Search .................................. 600/300, 301, 600/302, 513

(56) References Cited

U.S. PATENT DOCUMENTS

| | | |
|---|---|---|
| D247,251 S | 2/1978 | Napoli |
| 4,262,632 A | 4/1981 | Hanton et al. |
| 4,353,375 A | 10/1982 | Colburn et al. |
| 4,367,752 A | 1/1983 | Jimenez et al. |
| 4,543,955 A | 10/1985 | Schroeppel |
| 4,566,461 A | 1/1986 | Lubell et al. |
| 4,592,018 A | 5/1986 | Wiegman |
| 4,686,624 A | 8/1987 | Blum et al. |
| 4,803,625 A | 2/1989 | Fu et al. |
| 4,844,076 A * | 7/1989 | Lesho et al. |
| 4,883,063 A | 11/1989 | Bernard et al. |
| 4,909,260 A | 3/1990 | Salem et al. |
| 4,966,154 A | 10/1990 | Cooper et al. |
| 4,974,601 A | 12/1990 | Tranjan et al. |
| 4,987,897 A | 1/1991 | Funke |
| 5,002,064 A | 3/1991 | Allain et al. |
| 5,063,937 A | 11/1991 | Ezenwa et al. |
| 5,078,134 A | 1/1992 | Heilman et al. |
| 5,111,818 A | 5/1992 | Suzuki et al. |
| 5,113,859 A | 5/1992 | Funke |
| 5,128,552 A | 7/1992 | Fang et al. |
| 5,131,390 A | 7/1992 | Sakaguchi et al. |
| 5,137,345 A | 8/1992 | Waldorf et al. |
| 5,170,801 A * | 12/1992 | Casper et al. |
| 5,181,519 A | 1/1993 | Bible |
| 5,197,489 A | 3/1993 | Conlan |
| 5,199,439 A | 4/1993 | Zimmerman et al. |
| 5,213,106 A | 5/1993 | Lerner |
| 5,213,555 A | 5/1993 | Hood et al. |
| 5,218,969 A | 6/1993 | Bredesen et al. |
| 5,222,503 A | 6/1993 | Ives et al. |
| 5,226,424 A | 7/1993 | Bible |

(List continued on next page.)

FOREIGN PATENT DOCUMENTS

| | | |
|---|---|---|
| FR | 2686497 A1 | 7/1993 |
| GB | 9401040 A1 | 1/1994 |
| JP | 0299667 A1 | 1/1989 |
| WO | WO8802237 A1 | 4/1988 |
| WO | WO8905116 A1 | 6/1989 |
| WO | WO9413198 A1 | 6/1994 |
| WO | WO9424929 A1 | 11/1994 |

*Primary Examiner*—Scott M. Getzow
(74) *Attorney, Agent, or Firm*—Kudirka & Jobse, LLP

(57) ABSTRACT

A health monitoring system that monitors the health of a patient includes an ingestible capsule containing a medication to be consumed by a subject. A signal generator located within the capsule outputs an electrical signal having a predetermined characteristic indicative of said medication, said capsule and said medication being liberated by dissolution of the capsule in the stomach acid of a subject. A signal detector, preferably having an input in electrical contact with a portion of the subject's skin, is used to detects the electrical signal. This allows the ingestion of the medication to be tracked.

26 Claims, 27 Drawing Sheets

U.S. PATENT DOCUMENTS

| | | |
|---|---|---|
| 5,226,539 A | 7/1993 | Cheng |
| 5,228,450 A | 7/1993 | Sellers |
| 5,253,654 A | 10/1993 | Thomas et al. |
| 5,261,412 A | 11/1993 | Butterfield et al. |
| 5,271,405 A | 12/1993 | Boyer et al. |
| 5,275,159 A | 1/1994 | Griebel |
| 5,280,429 A | 1/1994 | Withers |
| 5,289,824 A | 3/1994 | Mills et al. |
| 5,307,263 A | 4/1994 | Brown |
| 5,447,164 A | 9/1995 | Shaya et al. |
| 5,454,376 A | 10/1995 | Stephens et al. |
| 5,792,048 A * | 8/1998 | Schaefer |

* cited by examiner

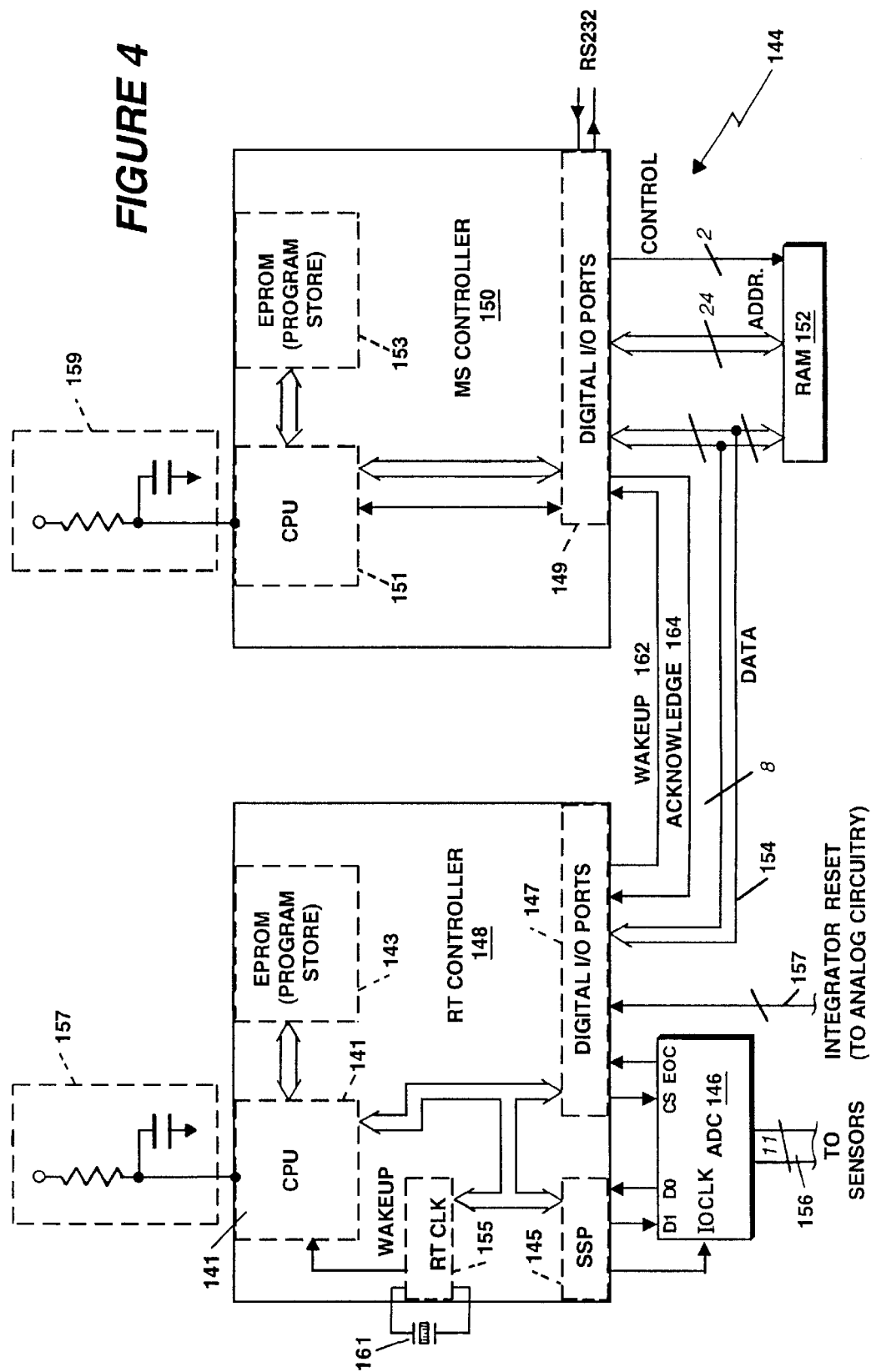

| GROUP | | BODY MONITOR SERVICE GROUPS |
|---|---|---|
| A | 2.5 KHz | EKG - Sample and Process |
| B | 100 Hz | Ventilation - Sample and Process<br>Acceleration - AC Sample and Process |
| C | 10 Hz | EKG - Pending Packet Transmission |
| D | 1 Hz | Breath Sound Integral - Sample and Process<br>Voice Sound Integral - Sample and Process<br>Acceleration - AC Integral Process<br>Acceleration - DC Integral Process |
| E | 1/min. | Record Barometer<br>Record Pectoralis Temperature<br>Record Underarm Surface Temperature<br>Record Ambient Temperature<br>Transfer Minute Packet to Memory<br>Reset Minute Packet Accumulators |

FIGURE 6

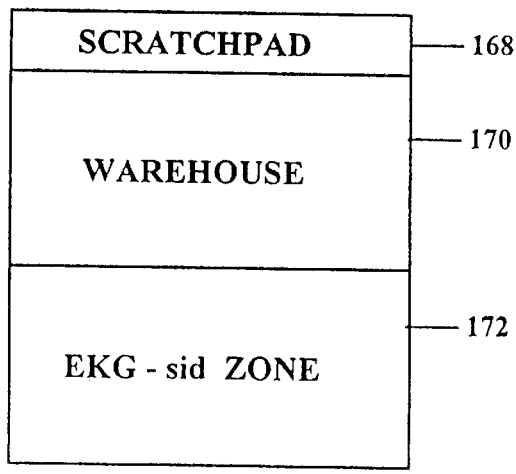

FIGURE 5

| MINUTE | 0 | 0 | 0 | 0 | 0 | 0 | 0 | 1 | + 31 BYTES |
|---|---|---|---|---|---|---|---|---|---|
| EKG -ts | 0 | 0 | 1 | P | X | X | X | X | + 2 BYTES |
| EKG - lid | 0 | 1 | P | X | X | X | X | X | + 1 BYTE |
| VENT - i | 1 | X | X | X | X | X | X | X | + 2 BYTES |
| EKG - sid | X | X | X | X | X | X | X | X | |

HEALTH MONITORING SYSTEM

CROSS REFERENCE TO RELATED APPLICATIONS

This application is a division of U.S. patent application No. 09/447,986, filed Nov. 23, 1999 now U.S. Pat. No. 6,282,441, which is a continuation of U.S. patent application No. 09/001,032 (now U.S. Pat. No. 6,095,985) filed Dec. 30, 1997, which is a continuation of U.S. patent application No. 08/394,157 (now U.S. Pat. No. 5,778,882), filed Feb. 24, 1995.

BACKGROUND OF THE INVENTION

1. Field of the Invention

The present invention relates to the field of medicine and health and, more specifically, to health tracking including assessing trends in health and the diagnosing and monitoring of medical conditions.

2. Description of the Related Art

In the medical profession today, the advent of high technology has provided a myriad of impressive diagnostic tools. However the focus of this medical technology has been on diagnosis of acute conditions, rather than advanced warnings and preventive advice. Routine "checkups" are the recognized method of monitoring a person's health. Such examinations provide a physician with information relating to the patient's condition. However, unless a patient's checkup is fortuitously scheduled for a time at which symptoms of an ensuing illness are just developing, the checkup may not be effective in helping to detect the onset of an adverse medical condition.

Portable health monitors have been developed in the past which monitor body parameters specific to a particular medical condition. In some cases these monitors record specific parameter data, while in others they provide an output to the patient which is indicative of the physical parameters they sense. Some monitors simply provide an alarm when the parameters reach a pre-set level of particular concern. Others, specifically some portable heart rate monitors, provide a digital display of heart rate to the patient. Still others record heart rate over time. Patients use such heart rate monitors to warn them of high heart rates. Athletes use them to ensure that their physical training includes periods of elevated heart rate thought to be sufficient to promote conditioning. Similar monitors also exist for measuring other parameters, usually individually or without the capability to store the information for extended periods of time.

SUMMARY OF THE INVENTION

Absent from the prior art is a portable monitor having the capability to construct, manage, and store a detailed, multiparametric, record of an individual's physiological and emotional well-being that can be used for tracking and assessing general health over days, months, and years. The present invention comprises a health monitoring system including a database and data management system linked with a plurality of health trackers, each of which regularly collects various forms of data about or from a patient/subject. The preferred embodiment of the invention consists of three basic components: 1) a data management system including the database; 2) a plurality of physiological and subjective data collection devices that collect a set of timestamped serial streams from a subject; and 3) a communications system by which the data is periodically uploaded from the monitors to the database.

In the preferred embodiment the health trackers each have a portable multiparametric monitor that automatically and noninvasively monitors physiological parameters. The health trackers each preferably also include a data logger that permits and/or prompts the patient to enter subjective reports of psychological and physiological data, as well as activities and environmental conditions. Thus, a composite stream (preferably serial) of objective physiological and subjective data is created which is indicative of the overall health history of a patient/subject.

In order to be effective as a prospective diagnostic tool, the information collected is not anticipatory of any specific medical condition, but is instead broadly related to the general health of the patient. That is, the data is collected from numerous health indicators or metrics, each of which may have some relationship, or may be completely unrelated to, any particular medical condition. The composite multiparametric data streams in combination provide enough information to allow the identification of a wide variety of possible trends in the tracking data which, as an ensemble, may be indicative of any of a variety of medical conditions. Although the data collected is not specifically related to tracking any particular condition, the entire system is designed so that patterns which are characteristic of healthy subjects, as well as ill ones, can be derived from the collected data.

The preferred embodiment of the data collection portion of the invention collects a combination of sensed physiological data and subjective data entered by the patient. For subjective data collection, the patient-supplied data is solicited by the data logger using data prompts, which may be in the form of health-related questions. These questions may include interactive input formats such as body diagrams or the like. As the data is collected, it is time stamped, compressed (where appropriate) and uploaded to the database, labeled for the patient in question. The resulting health history is a combined format of objective physical parameters and subjective patient data which is time-indexed for subsequent retrieval and analysis. From these stored datastreams, trends in the data may be identified.

Each health tracker includes a means for periodically uploading the collected data to the database. In the preferred embodiment, the health trackers communicate with the database via a public information network. The monitors are connected to the network by a communications device such as a modem. Once stored in the database, the data may be later accessed by an authorized physician or by the patient. Because the data is logged by patient and time-index, the data can be recovered for a particular patient and a particular time period with relative ease. The data stored by the present invention in the database is of particular value for identifying trends in healthy persons due to the fact that it is collected regularly, irrespective of the patient's medical condition. The invention thus provides a powerful tool previously unavailable to physicians for the early detection of adverse medical conditions.

The multiparametric physiological monitor is a portable unit for continuous monitoring of certain physical parameters of the patient. In the preferred embodiment, the monitor sensors include EKG electrodes, a chest expansion sensor, an accelerometer, a chest microphone, a barometric pressure sensor, an underarm temperature sensor, a pectoralis temperature sensor and an ambient temperature sensor. Each of the sensors provides an output signal to an analog-to-digital converter (ADC) which is controlled by a real-time (RT) controller. The RT controller is preferably a digital microcontroller which runs a program that collects data from the sensors and transmits the collected data to a second controller, referred to as the "memory server" (MS) controller, to be stored.

The MS controller, like the RT controller, is preferably a digital microcontroller. The MS controller runs a program that compresses the data received from the RT controller, where appropriate, and stores it in a random access memory (RAM). In addition, the MS controller is responsible for communications with external entities such as a database server.

In the preferred embodiment, electrocardiogram (EKG) data is reduced and compressed, and ventilation (chest expansion sensor) data is reduced. The ventilation data is reduced by storing a series of time interval/amplitude pairs that comprise a straight-line approximation of the chest expansion signal. The straight-line approximation uses the significant events in this signal, such as the inflection points in the breathing is cycle, and the start and stop of breathing plateau periods (i.e. extended times of stable chest circumference), as well as sharper inflections associated with sneezing, coughing or retching.

EKG data, sampled most frequently, is reduced by storing only timing information for each heartbeat (QRS complex) and, once per minute, storing the median values of various components of a straight-line approximation of the QRS complex. The heartbeat interval information is compressed by storing the differences in interval duration rather than the interval itself where possible, and storing the interval differences in formats which take advantage of their compressed size.

The RAM is divided into three regions: 1) the scratchpad; 2) the warehouse (long-term storage of all but 8-bit EKG data); and 3) the 8-bit EKG data area. As data is received, it is placed in the scratchpad. As time permits, data is read from the scratchpad, processed, and stored in the warehouse or the EKG zone, depending on the data type and size. The MS controller stores data received from the RT controller in the scratchpad in the packetized format in which it was received. When not busy with other tasks, the MS controller processes data temporarily stored in the scratchpad and places it in variable-length fields in the warehouse or fixed-length fields in the EKG zone. The data in the warehouse is tagged using a coding method which identifies the data type with a particular sequence of leading bits. This allows proper reassembling of data as it is read out of memory.

In the preferred embodiment, the subjective data logger runs a user-friendly data collection program which prompts the patient to report subjective data or simply serves to structure a voluntary submission of a report. This data is timestamped and stored in a local memory unit of the data logger for later uploading to the database. The monitor and the data logger may be linked together to connect to the database as a single unit via a public data network or other communication medium. Alternatively, either of the monitor and the data logger may individually connect to the database.

One particular feature of the present invention involves the use of a capsule which contains a patient's medication, along with a miniature pulse generator and transmitter. When the capsule is ingested and dissolves in the patient's stomach acid, the medication is liberated and the transmitter is activated. The transmitter transmits a pulsed signal which is uniquely identified with the medication in the capsule. The signal is detected by the EKG electrodes of the monitor on the surface of the patient's skin, and is decoded by the monitor firmware to automatically identify which drugs are ingested by the patient and when they are taken.

BRIEF DESCRIPTION OF THE DRAWINGS

FIG. 4 is a schematic depiction of the hardware of a portable multiparametric monitor of the present invention.

FIG. 5. is a memory map of the RAM memory of a portable multiparametric monitor of the present invention.

FIG. 6 is a table of the service groups for data collected by a portable multiparametric monitor of the present invention.

FIG. 7 is a representation of how data is stored in RAM.

FIG. 19A depicts a "side effects" screen display of the subjective data logger.

DETAILED DESCRIPTION OF A PREFERRED EMBODIMENT

Figure 1:
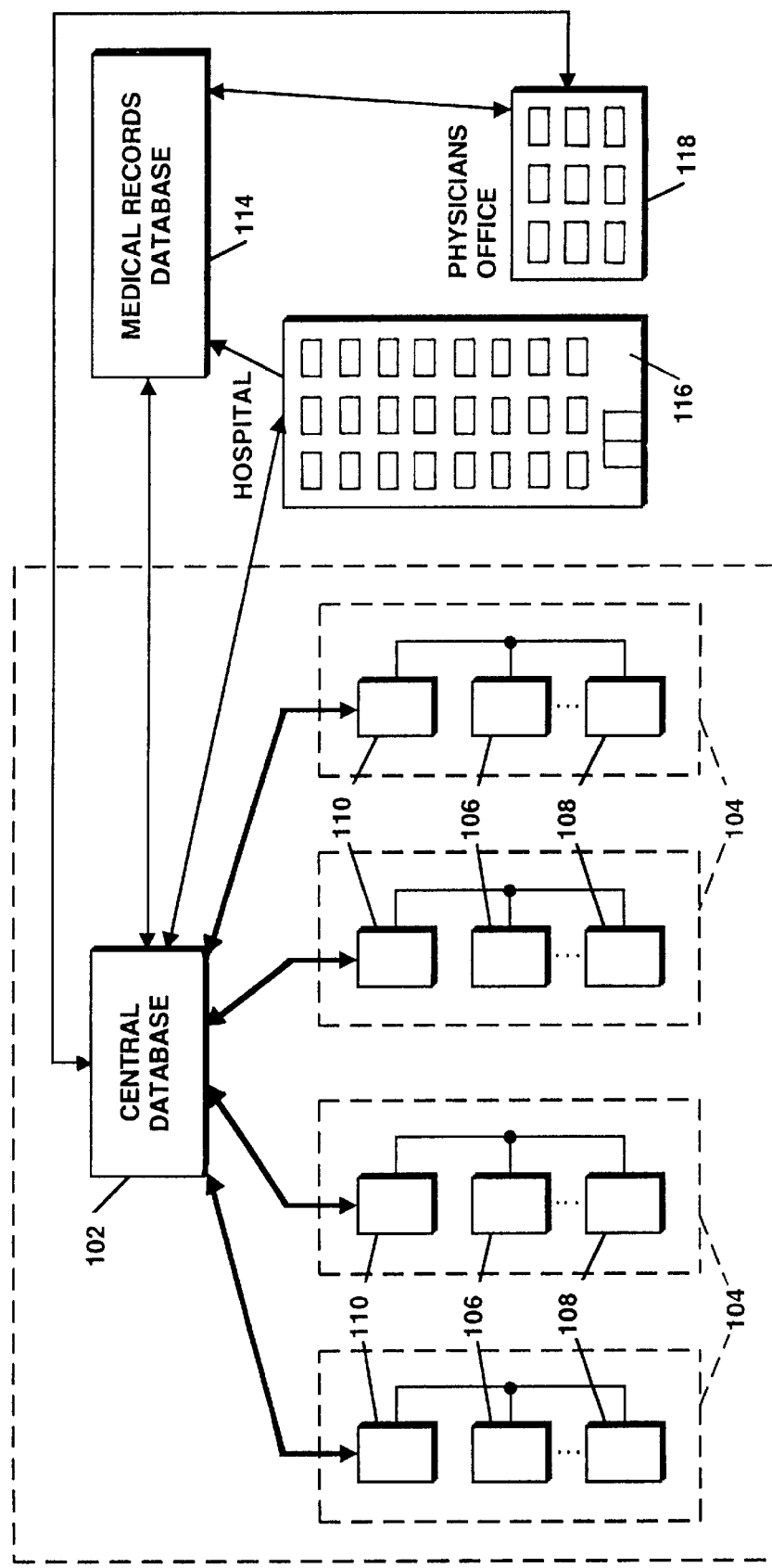
FIG. 1 is a schematic overview of a health monitoring system in accordance with the present invention.

Shown in FIG. 1 is a health tracking system 100 which has a central database 102 with a data link connectable to each of a plurality of health trackers 104. In the preferred embodiment, each of the health trackers 104 includes a multiparametic physiological monitor 108 and a subjective data logger 106. In the preferred embodiment the monitor 108 connects directly to a modem 110 (when used without a data logger 106), or can be connected to a serial data port on the subjective data logger which, in turn, connects to a modem 110. In the preferred embodiment an external modem is used primarily because of lower cost, however those skilled in the art will recognize that it would also be possible to include a single chip modem in the monitor 108 or to plug a PCMCIA modem into the data logger 106. The external modem of the preferred embodiment also includes a chargepad for recharging the batteries of the portable monitor 108 and data logger 106 units.

The monitor 108 and the data logger 106 collect data from the patient which is time stamped and stored locally for later uploading to the central database 102. Those skilled in the art will recognize that the "central" database may actually be a plurality of databases. However, for the purposes of this description, the database will be described as a single unit.

Preferably, the data link from each of the health trackers 108 and each of the data loggers 106 to the database is established using an associated modem 110, and some combination of a telephone network and a data network. In the present embodiment, the modem 110 directly connects via telephone to one of the computers that support the database 102. In the alternative, the modem may connect to a local network access computer and transmit data to the database via the network connection. Those skilled in the art will recognize that there is a variety of means to transfer data from site to site, and that different means may be chosen at anytime based on cost and convenience.

The monitor 108 collects objective data on the patient's physical condition via a plurality of automatically-controlled physiological sensors. The subjective data logger collects subjective information from the patient by providing the patient with an input device having data prompts such as questions regarding the patient's condition. Within the context of this description, the term "objective" data will refer to that data which is obtained by sensing the patient's physiological parameters. Correspondingly, the term "subjective" data will refer to that data which is input by the patient to the data logger 106, regardless of whether that data pertains to the patient or the patient's environment, and whether or not the information is objective or factual, such as medication dosage or consumption of a particular food.

Referring to FIG. 1, a medical records database 114 contains information regarding patient medical histories. Also shown graphically in FIG. 1 is a depiction of a hospital 116 and a physician's office 118. The hospital 116 and physician's office also have data connections with database 102 to allow the transfer of data to and from the database. In addition, the database 102 has a direct connection to the medical records database to allow the transfer of information directly between the two locations. Although only one hospital building and one physician's office are shown in the figure, those skilled in the art will recognize that there can be, and are likely to be, a large number of hospitals and physicians offices with communications links to the medical records database 114. In addition, a number of personnel not directly related to patient care may be located at these and other sites, similarly connected over a public or private network, who will be performing data management and analysis services.

Multiparametric Monitor

Figure 2:
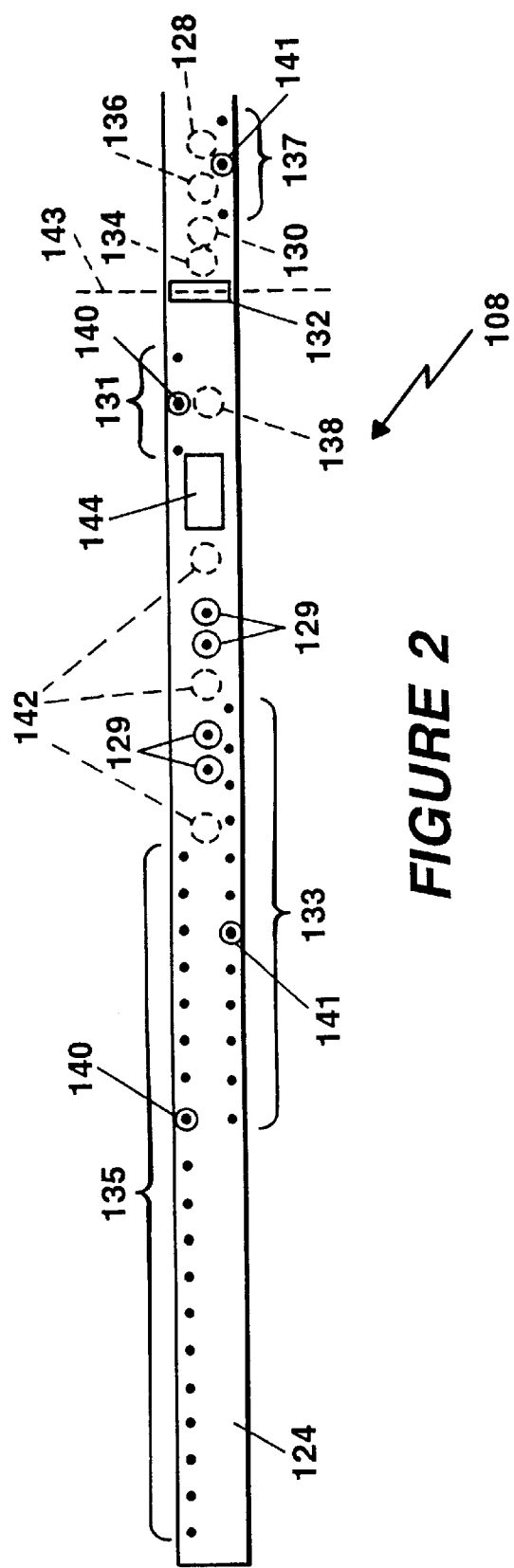
FIG. 2 is a front view of a portable multiparametric monitor which is part of a preferred embodiment of the present invention.

Shown in FIG. 2 is multiparametric monitor 108. The monitor 108 comprises a body strap which, in the preferred embodiment, is a chest strap 124 upon which are distributed various sensors and supporting electronics. (It will be recognized by those skilled in the art that a multiparametric monitoring device may also be mounted by a strap about a part of the body other than the chest). As shown in the top view of FIG. 2A, the chest strap 124 fits around the torso of a patient 120. In the preferred embodiment, all of the electronics and sensors are configured in the flexible strap itself such that the monitor is completely self-contained. That is, the chest strap 124 includes a number of flexible conductors which are embedded in the strap. The various components are mounted in the strap, and are interconnected via the embedded conductors. In the preferred embodiment, the belt, sensors and accompanying electronics have a thin profile, and the strap is a consistent 0.9 inches wide along its length. Most of the monitor is less than 0.20 inches thick, except for an area containing the batteries 129 and an area containing the chest expansion sensor and accelerometer, each of which is approximately 0.3 inches thick.

Figure 2A:
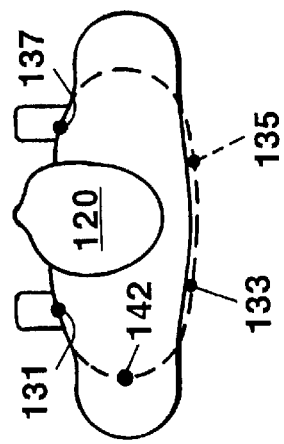
FIG. 2A is a top view of a patient wearing the multiparametric monitor which shows the desired locations of EKG electrodes of the monitor.

A variety of parametric sensors are supported by the monitor, each being located on the strap 124 as most appropriate for the parameter (or parameters) which it detects. Each of the sensors provides an electrical input to analog circuitry which filters and amplifies the sensor signals, as known in the art of signal processing, and outputs them to an analog-to-digital converter, which is part of monitor hardware 144. The hardware 144 of the monitor 108 receives data from the sensors in a manner which is discussed in detail with reference to FIG. 4. The identification of the following sensors in FIGS. 2 and 2A is intended to describe a preferred embodiment for the sensors and their locations relative to the patient's body, and is not intended to limit the use of other sensors or other positioning of sensors with the present invention.

Figure 3:
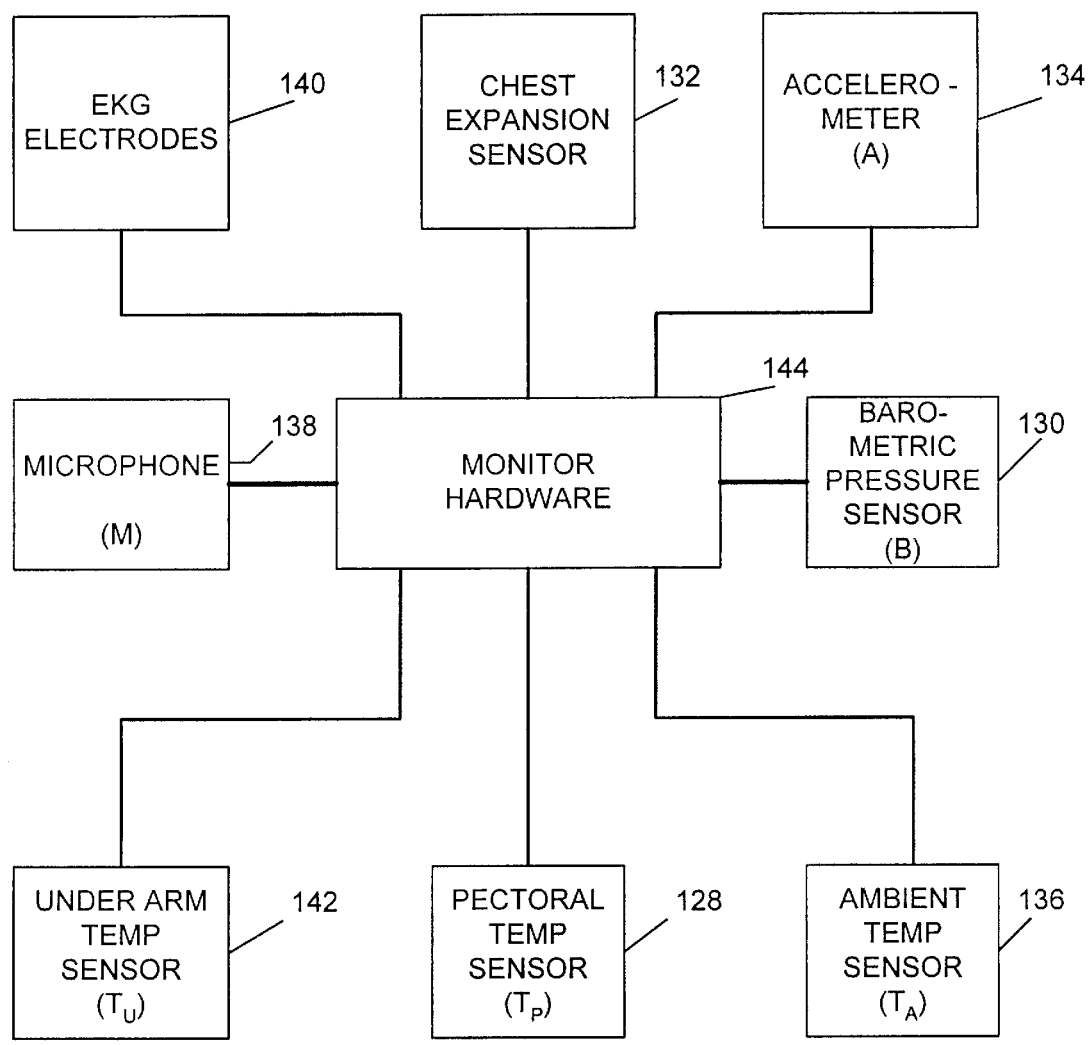
FIG. 3 is a block diagram of a portable multiparametric monitor of the present invention.

The sensors (shown in block diagram form in FIG. 3) are as follows: pectoralis temperature sensor 128, which senses the temperature of the surface of the patient's chest; barometric pressure sensor 130, which senses the ambient barometric pressure of the patient's environment; chest expansion (ventilation) sensor 132, which detects the tension on the chest strap 124 as an indication of the expansion and contraction of the patient's chest; accelerometer 134, which detects movement and inclination of the patient's body; ambient temperature sensor 136, which senses the ambient temperature of the patient's environment; microphone 138, which detects sounds from within the patient's torso; and underarm temperature sensor 142, which senses the temperature of the side of the patient's torso underneath the arm. Also on the chest strap 124 are EKG electrodes 140, which detect electrical signals caused by action of the heart muscle.

In the preferred embodiment, two EKG electrodes 140 and two ground, or reference, electrodes 141 are placed in contact with the skin of the patient's chest, and detect electrical signals generated by the pumping action of the patient's heart muscle. The EKG (electrocardiogram) is an indication of the patient's heart activity, as is well known in the field of medicine. The EKG signal acquisition circuit is of known design and produces an EKG signal which is sampled periodically under control of the monitor hardware.

Referring to FIG. 2, the electrodes 140, 141 are each a made of a conductive rubber and have a metal pin projecting from a back side. The back side is also provided with an adhesive coating which allows the pin to be plugged into the outer surface of the strap 124 and retained along the surface by the adhesive. For each of the electrodes 140, 141, a plurality of conductive, locking receptacles 131, 133, 135, 137 are equally spaced along the surface of the strap 124. Each set of receptacles 131, 133, 135 137 is a common electrical point established by a conductor embedded in the strap 124 (e.g. all receptacles in the group marked 135 are electrically connected, but are isolated from the receptacles 131, 133 and 137).

Each of the receptacle groups 131, 133, 135, 137 provides one input to the hardware 144. By plugging a pin 140, 141 into a particular receptacle of a group, the location of that pin is established relative to pins which are similarly plugged into receptacles of other groups. This relative location of EKG electrode and ground pins 140, 141 allows the chest strap 124 to be adapted to the different sized torsos of different patients. The correct location of the pins can be determined by considering the desired locations of the electrodes and ground points relative to the patient's body.

FIG. 2A shows the preferred locations of the electrode and ground pins 140, 141 relative to the body of a patient 120. The reference numerals pertaining to each of the receptacle groups are used to indicate these locations. As shown, in the preferred embodiment, electrode pins 140 are located in receptacle groups 131 and 135, while the ground pins 141 are located in receptacle groups 133 and 137.

To determine the receptacles to which each pin 140, 141 should be connected in its respective group, the chest strap 124 is first aligned relative to the patient's body by locating sternum center line 143 directly in front of the patient's sternum. The strap is then wrapped around the patient's torso, and the receptacles on the strap which are closest to the locations 131, 133, 135 and 137 shown in FIG. 2A are selected as the proper insertion points for the pins 140, 141. Although different patients have different sized torsos, the varied receptacle locations for each group 131, 133, 135 137 nonetheless is allow for a distribution of EKG contacts as shown in FIG. 2A for each patient. Those sensors of the monitor other than the EKG sensor are discussed briefly below.

The chest expansion sensor 132 is a tension sensing device which senses the change in tension on the chest strap 124 of the monitor 108. In the preferred embodiment, the chest expansion sensor 132 includes a strain or stress gauge, which has an output that changes with the tension on the chest strap 124. As shown in FIG. 2, the chest expansion sensor is located right at the sternum center line 143 of the chest strap 124.

The accelerometer 134 uses a well-known piezo-resistive bridge sensor, and is located within the chest strap 124. The output of the bridge sensor is amplified and filtered to separate the AC and the DC components. Each of the AC and DC signals is then individually sampled by the monitor hardware.

Microphone 138 is located on the side of the monitor 108 facing the patient's chest so that it remains in contact with the chest cavity. The audible signals detected by the microphone are amplified in a pre-amplification stage and then divided along separate circuit paths which develop the "breath sounds" signal and the "voice sounds" signal, respectively. The breath signal path incorporates a bandpass filter passing frequencies in the range 1.5 KHz–5 Khz.

Similarly, a voice signal bandpass filter ranges from 600 Hz–2 KHz. In the preferred embodiment, simple RC filters are used, as is known in the art of circuit design. Those skilled in the art will recognize that other designs for said filters can be implemented without significantly affecting the form and function of the device. Separate output paths are provided for the different signals to allow them to be sampled on different channels of the analog-to-digital converter 146.

In addition to providing the breath signal output and the voice signal output, additional circuitry provides for analog integration of each of these signals. The integrator circuits used with each branch are standard analog integrators, well known in the art, which are reset periodically so as to provide an appropriate integration time. For each of the breath integral and the voice integral, the reset signal for restarting the integration cycle is generated once each second by the monitor hardware immediately after sampling the signal in question.

The barometric pressure sensor 130 is located on the side of the chest strap 124 away from the patient's body. The pressure sensor 130 is of known design and uses a piezo-resistive bridge sensor. The output of this sensor is amplified and sampled by the monitor analog circuitry and hardware once a minute.

Each of the underarm, the pectoralis and the ambient temperature sensors use an amplifier having a thermistor-controlled feedback loop to generate a temperature output signal. The thermistor for each is packaged in a waterproof protective sleeve and is located adjacent to the area in which it senses temperature. The underarm thermistor is located adjacent to the patient's torso with its protective package in contact with the patient's skin. Similarly, the pectoralis thermistor is located on the inside of the chest strap 124 such that its protective package contacts the patient's skin in the center of the chest, where the housing 122 is located. The ambient thermistor is located on the side of the chest strap 124 away from the patient's body. It gives an indication of the patient's thermal environment, and allows a comparative analysis with the other temperature sensor outputs.

The monitor hardware 144 is shown in block diagram form in FIG. 4. The hardware 144 includes a real-time (RT) controller 148 which coordinates the sampling of the sensor outputs, organizes the data into an appropriate format and transmits it to the memory server (MS) controller 150 for later uploading to database 102 (FIG. 1). The analog output of each of the monitor sensors from the analog circuitry of the device (shown as inputs 156 in FIG. 4) is connected to an analog-to-digital converter (ADC) 146. There is also an set of integrator reset lines 157 which the RT controller uses to reset the integration circuits of various monitor circuitry. In the preferred embodiment, the ADC 146 is a twelve-bit, serial digital interface converter such as the TLC2543. Those skilled in the art will recognize that use of a different type of converter or one with different resolution will not significantly affect the form or function of the invention.

RT controller 148 is an interrupt-driven microcontroller, such as a Microchip PIC16C74, which runs a program (firmware) that will be discussed in more detail hereinafter. The RT controller 148 is responsible for the data sampling and pre-processing. The MS controller 150 (also an interrupt-driven microcontroller) is responsible for receiving the data packets from the RT controller 148, compressing the data, where appropriate, and storing it in the appropriate part of random access memory (RAM) 152. The MS controller 150 is also responsible for controlling the flow of data between RAM 152 and external entities such as the database 102 (FIG. 1), or subjective data logger 106. While the preferred embodiment uses two Microchip PIC16C74 microcontrollers, those skilled in the art will recognize that it would be possible to use different controllers or processors from the same or other vendors, or even to perform both functional groups (the real-time block and the memory server block) in a single microcontroller without significantly affecting the form and function of the invention.

Each of the controllers 148, 150 includes a number of internal elements which, in the preferred embodiment, are integral components of the integrated circuits which comprise the controllers 148, 150. The RT controller 148 has a central processing unit (CPU) 141 which runs a firmware program stored in a "program store" which, in the present embodiment, is erasable, programmable read-only memory (EPROM) 143. In executing the stored program, the RT controller provides the necessary control signals to collect data samples using the ADC 146 and to transmit the collected data to the MS controller 150.

The RT controller 148 includes a synchronous serial port (SSP) 145 via which CPU 141 provides commands to the "data in" (DI) port of ADC 146, and receives data from the "data out" (DO) port of ADC 146, controlling the data transfer using a clock signal "IOCLK". The communication between the RT controller 148 and the ADC 146 is bi-directional and synchronous, that is, data is transmitted both directions simultaneously with each pulse of signal "IOCLK". Those skilled in the art will recognize that the communication arrangement is specific to the ADC 146 in the implementation and may be changed to accommodate another type of ADC without significantly affecting the form and function of the invention.

To acquire data from a particular channel, the RT controller 148 transmits a serial control message to ADC 146. Included with this message is a four-bit code indicating which of the eleven analog input lines is to be sampled. The ADC 146 then latches the analog signal on the specified line, and begins converting it to a 12-bit sample. When the sample is complete, the ADC 146 provides an output on pin "EOC" (end of conversion) which is detected by CPU 141 at one of the digital I/O ports 147 of RT controller 148. This signal indicates to the RT controller 148 that data is available to be read from the ADC 146, and that the ADC 146 is ready to perform another conversion. Under control of the RT controller 148, the sample is then transmitted from the DO port on the ADC 146 to the "data in" (DO) pin of SSP 145 of RT controller 148.

Each of the controllers 148, 150 is a low-power device which has a power-down (or "sleep") mode in which most of its power consuming components are de-energized until an electrical "wakeup" signal is received at the appropriate input port. Such power saving strategies are a key element to allowing the physiological monitor to make use of small, light batteries, and thus be unobtrusive to wear, while still being capable of "real time" processing as required for the invention.

Although prior art real-time, intermittent devices exist, they typically have relatively long delays between the times at which they were "awakened." This long delay is necessitated by the requirement of a crystal clock source, which gives the accuracy necessary for real-time processing. The delay is a result of the fact that crystal oscillators typically require more than 1000 clock cycles to properly stabilize. Thus, if a crystal oscillator were turned on and off with each intermittent cycle of the present invention, the monitor would be limited to a much lower sampling rate, and the resolution of the system would be significantly lower.

RC oscillators (i.e. those which make use of a resistive/capacitive network) are traditionally not favored for real-time devices because of their inherent inaccuracy. In order to provide a high resolution system, while reaping the low power benefits of intermittent operation, the present invention uses multiple clocks, each directed toward a different task. These clocks include real-time (RT) clock 155, and RC instruction clocks of the CPUs 141, 151 which make use of external RC circuits 157, 159.

While most of the elements of the RT controller 148 and the MS controller 150 are idle during "sleep" cycles, the RT clock 155 runs continuously, at a rate of approximately 32.5 KHz (In the preferred embodiment, the crystal is a "watch crystal" which runs at a speed of 32,768 Hz, but for the remainder of the description will be discussed in terms of the approximate 32.5 KHz speed). The RT clock 155 makes use of a crystal 161 (such as quartz crystal), which ensures accurate oscillation of the clock circuit. The RT clock includes a timer which every thirteenth oscillation provides a "wakeup" pulse to CPU 141. The wakeup pulse causes the CPU to come out of its idle state, and to initiate a sampling event. Thus, the wakeup pulses are generated at a frequency of 2.5 KHz, the desired maximum sampling frequency of the system.

Although the periodicity of the wakeup pulses (and therefore the sampling rate of the system) is rigidly controlled by the crystal-based oscillator of the RT clock 155, the CPU clock (which must be much faster than the 2.5 KHz rate of the RT clock 155) is controlled by the RC pair 157. This RC clock is not a precision clock, but provides an oscillation rate of approximately 4 MHZ. This comparatively fast clock speed allows the CPU 141 to process all of the instructions necessary to accomplish the desired data transfer tasks involved in signaling the ADC 146, receiving data from the ADC 146 and transmitting the data to the MS controller 150. Indeed, this clock speed is sufficiently fast that the RT controller is able to finish the interrupt service well before the next wakeup pulse from the RT clock 155 arrives, thus allowing it to return to "sleep" mode or to be in an interruptible background processing mode. Although the RC-based clock is significantly less accurate than the RT clock, the data processing tasks do not require a highly accurate clock. Because the RT clock 155 synchronizes each data sampling event by initiating the data collection sequence with a wakeup pulse, the maximum sampling rate is a stable 2.5 KHz.

The dual-clock feature of the present invention allows for full digital event detection of heartbeat (QRS) signals with intermittent operation of the controlling processors. Unlike earlier intermittent devices (in which events such as QRS complexes were detected by external, analog circuits that, in turn, "awakened" the processor), the RT controller 148 detects the QRS events digitally by using "fine-grain" intermittent operation, in which the processor "wakes up" every 400 $\mu$s to sample and process the EKG signal. This differs from the "coarse grain" intermittent operation of prior systems in which the processor wakes up to process an externally detected event (typically no more often than 100 times per minute). This fine grain operation is made possible by using the RC oscillator as a clock source, which allows the processor to begin useful operation within one or two clock cycles (0.25 to 0.5 $\mu$s) of getting a wakeup signal.

After a full data packet is ready for transfer, the RT controller 148 alerts the MS controller 150 that it is ready to begin transmitting data by providing an output on one of its digital ports 147 which is received on one of the digital ports 149 of MS controller 150. This signal interrupts or, in the case that it was idle, "wakes up" the MS controller 150 and causes it to prepare for the data transfer. The CPU 151 of the MS controller 150 runs a firmware program stored in the EPROM program store 153. When not servicing the RT controller data, the MS controller 150 is either post-processing data previously received from the RT controller 148 (i.e. performing data compression or storing data to RAM 152), or is powered down in a "sleep" mode.

The sleep mode is essentially the same as the sleep mode of the RT controller. As part of the program of the MS controller 150, in order to conserve power in the system, the CPU 151 de-energizes most of the MS controller 150 circuits when there are no postprocessing tasks or servicing required for RT controller data. The MS controller is "awakened" by the receipt of the wakeup pulse from RT controller 148 along line 162, in the same manner that the RT controller 148 is "awakened" by the wakeup pulse from the RT clock 155.

Upon receiving the wakeup signal, the MS controller 150 either powers up (if in sleep mode), or suspends its post-processing activities in order to provide service to the RT controller 148. Once ready to receive data, the MS controller 150 sends an acknowledgment signal to RT controller 148 on protocol signal line 164. Further interaction between the RT controller 148 and the MS controller 150 occurs over bus 154 and is arbitrated by protocol signals 164 and 162. Those skilled in the art will recognize that the general manner of communication between the controllers is well-known in the art and that changes to the particulars thereof do not significantly affect the form or function of the invention.

The RT controller 148, in its request, indicates to the MS controller 150 what type and how much data it will be transmitting. Once the RT controller request is acknowledged, the MS controller coordinates data transfer from the RT controller 148 to the RAM 152. Synchronization between RT controller 148 and MS controller 150 is accomplished using protocol signals 164 and 162. While data is synchronously transmitted over bus 154, RAM 152 is controlled directly by MS controller 150. When the transfer is completed, the RT controller 148 resumes its data collection tasks, and MS controller 150 resumes its post-processing tasks.

Prior to post-processing (i.e. when the monitor data is first transmitted from RT controller 148), newly-received data is placed in the "scratchpad" of RAM 152 by the MS controller 150. As shown in the memory map of FIG. 5, in the preferred embodiment, the scratchpad 168 occupies a fixed amount of separate memory which, in the preferred embodiment, is 2,304 bytes. After post-processing, the resultant data will be stored in either the warehouse 170 or the 8-Bit EKG-sid zone 172. Where any particular monitor data is stored in RAM 152 depends on the type of data in question. As described below, different types of data are handled differently by the firmware of the present invention.

FIG. 6 is a table of monitor 108 service groups. Each service group is defined by the rate at which subroutines are run and/or data samples are taken for the monitored parameters of the group. The different sampling rates shown in the figure are selected as part of the preferred embodiment, and are based on numerous factors including, but not limited to: 1) the necessary minimum sampling rate to properly characterize the sensor signal in question; 2) the desired frequency of samples for creating a data history for the sensor signal in question which is of the most value in detecting trends and diagnosing medical conditions; 3) the processing speed limitations of the system hardware; and 4) the practical limitations on the memory storage capabilities of RAM 152 and of the database 102. It will be apparent to those skilled in the art that different service groups and different sampling rates may be used as an alternative embodiment of the present invention.

Referring to FIG. 6, the most infrequently collected data is in Group E, referred to as "minute" data. Included in this group are sensor signals which change relatively slowly with time. Specifically, this group includes: 1) the barometer signal; 2) the pectoralis temperature sensor signal; 3) the underarm temperature sensor signal; and 4) the ambient temperature sensor signal. Each of the se signals is sampled by the RT controller 148 once every sixty seconds. In addition to the sampled signals, the service group table of FIG. 6 also shows other functions performed once a minute as part of Service Group E. These functions include transferring a stored "minute (data) packet" to RAM 152 and resetting minute data packet "accumulators," which are selected memory locations maintained by RT controller 148.

Because the minute data is collected relatively infrequently, no data compression is performed on this data, and it is stored essentially "as is." For convenience, in the preferred embodiment, all of the data which is collected once a minute is stored together as part of the "minute packet," along with other data which is computed on a once per minute basis. Thus, all of the stored data for a particular "minute" is identified by a single timestamp. The various components of the minute packet are discussed in more detail hereinafter with regard to the data packet structures shown in FIG. 7.

Referring again to FIG. 6, the next most infrequent group of collected data is the 1 Hz group (Group D), for which data samples are collected at the rate of one per second. The data collected as part of this service group is used to compute values that are stored as part of the minute packet. Within this service group are the processing of a breath sounds integral and a voice sounds integral. As discussed previously, the analog circuitry for each of the microphone-based signals includes a conventional integrator circuit which integrates the detected signal over time. The breath signal and the voice signal are each allowed to integrate over the period of one second and, as part of the 1 Hz service group, the integrators are reset after the integrated data is collected.

Other data which is collected and processed once per second are the AC and DC acceleration integrals and the activity duty cycle value. The signal from accelerometer 134 is collected as part of a 100 Hz service group (Group B), but those collected samples are not stored in RAM 152. Instead, the software run by the RT controller 148 mathematically integrates (accumulates) the 100 samples over a period of one second. Two types of integrals are calculated, the AC integral and the DC integral. The DC integral is the average DC value of the samples collected over the last minute, and is indicative of the relative orientation of the patient's body. The AC integral is an average change in the signal per unit time, and is indicative of the level of physical activity of the patient. In addition to these values, an activity duty cycle value is calculated each minute which is a number between 0 and 59. This number corresponds to the number of seconds in a given minute where the absolute value of the AC acceleration integral exceeds a pre-set threshold value, thus giving an indication of relatively active behavior as opposed to relatively inactive behavior.

Group C in FIG. 6 is the 10 Hz signal group, and includes the function of transmitting any pending EKG data packets to the MS controller 150 for storage in the appropriate section of RAM 152.

The 100 Hz group (Group B) includes the sampling of the ventilation (chest expansion sensor 132) signal and the sampling of the accelerometer 134 signal. Prior to transmission to MS controller 150, the ventilation signals are subjected to a reduction algorithm which operates on the collected ventilation samples. This data reduction is discussed in more detail hereinafter.

The most frequent data sampling group is Group A, the 2.5 KHz group. This service group is dedicated to the collection of EKG data. Because of the importance of EKG data and the rapidly changing nature of an EKG signal, the 2.5 KHz sampling rate is preferred. However, this relatively high rate of data collection results in a large number of data samples which, if stored "as is," would consume a great deal of memory space in RAM 152. For this reason, the data is reduced by RT controller 148 and further compressed by MS controller 150 to change the form of the data to one which consumes a much smaller amount of memory. This data compression technique is discussed in more detail hereinafter.

The structure of the data packets for storing the data collected by the body monitor 108 are depicted schematically in FIG. 7. In the preferred embodiment, five different data packet structures are used to store the following types of monitor data: "minute" data; "EKG-ts" (EKG-"timestamp") data; "EKG-lid" (EKG-"large interval difference") data; "vent-I" ("ventilation interval") data; and "EKG-sid" (EKG-"small interval difference") data.

To allow the different data packets to be distinguished when they are later read from memory, the preferred embodiment relies on an encoding algorithm, along with segregated memory locations in RAM 152. The data encoding of the present invention relies on a logical "1" being positioned within the first byte of the packet in a specific position relative to the most significant bit (MSB) of that byte, with leading logical "0" s stored in any vacant preceding bits. The location of the first logical "1" relative to the MSB indicates the type of data which is to follow.

In the present invention tags are assigned to the various fields primarily based on frequency of use, and secondarily based on which allocation would permit all packets to fit in the smallest number of 8-bit fields. For example, the ventilation packet has the shortest tag (a one with no leading zeros) even though it is less frequent than the EKG-lid packet. However this allocation permits the ventilation packet to be stored in three bytes and the EKG-lid packet to be stored in two bytes. While changing the allocation of tags between these two packet types would still require two bytes for the EKG-lid packet (with some unused bits), it would also require four bytes for the ventilation packet. An additional advantage is provided by locating the most frequent fields of all, the EKG-sid fields, in a different portion of memory, with no tag field at all (as discussed below)

As shown in FIG. 7, each of the data types has a logical "1" in a different location in its first byte, except for the EKG-sid data packet. The EKG-sid data does not require an encoded label because it is stored in the eight-bit EKG-sid zone 172 of RAM 152 (FIG. 5), separate from the remaining data types. While minute data, EKG-ts data, EKG-lid data and vent-I data is all stored in warehouse 170 (i.e. hexadecimal memory locations 0x100 and above) starting with the lowest memory address and progressing toward higher addresses in memory, EKG-sid data is stored in EKG-sid zone 172 starting with the highest memory address allocated to EKG-sid data in RAM 152 and progressing toward lower addresses in memory. In the preferred embodiment, there is no fixed border between the warehouse 170 and the EKG-sid zone 172. If there is a data collision between the warehouse 170 and the EKG-sid zone 172 (i.e. if all of the memory in RAM 152 is filled), an error is detected and the MS controller 150 discontinues the data storage process. All data already stored in these two zones is retained.

Referring again to FIG. 7, the minute data packet has a first byte which is all leading logical "0"s, except for the least significant bit (LSB). This first byte is a label for use in reading data out of memory which indicates that the next thirty-one bytes of data stored in the warehouse are minute data. These thirty-one bytes are occupied as described below.

The first four bytes of the minute data packet contain "TIMESTAMP," a timestamp for the data collected during the minute in question. The next three bytes contain "COUNT," "ECOUNT" AND "VCOUNT," respectively. COUNT is a sequence number of the current minute packet, modulo 256. That is, an eight-bit counter is incremented with each minute packet. The counter provides a reference label for each minute packet, and rolls over every 256 packets. ECOUNT is the total number of EKG packets sent by the RT controller 148 during the last minute, from 0 up to 255. In the event that more than 255 EKG packets are sent, the number 255 will be reported. VCOUNT is the total number of ventilation packets sent by the RT controller 148 during the last minute.

The next two bytes of the minute packet are EKG__DEPOL and EKG__REPOL, respectively. EKG__DEPOL contains the median EKG depolarization value over the last minute and EKG__REPOL contains the median repolarization value over the last minute. These are followed by one-byte field EKG__RETURN, which contains the average up-slope width of the EKG pulses resulting from the heart muscle contraction.

The EKG fields are followed by two-byte field BARO__PRES (the barometric pressure), and four values derived from the sampling of the activity sensor (i.e. the accelerometer): ACTV__INTG (the activity integral—two bytes); ACTV__MAX (the maximum value of the accelerometer signal over the last minute—two bytes); ACTV__DCYC (the average duty cycle of the accelerometer signal over the last minute—one byte); and ACTV__INCL (the average inclination of the patient over the last minute as determined by the DC integral of the accelerometer signal—two bytes).

The next two fields of the minute data packet are VOICE__INTG (the integral of the detected voice signal—two bytes) and VOICE__DCYC (the duty cycle of the voice signal—one byte). Next are the BREATH__INTG (two bytes) and BREATH__DCYC (one byte), representing similar quantities for the breath sounds signals. These are followed by three two-byte fields: T__PEC (the pectoralis temperature); T__ARM (the underarm temperature); and T__AIR (the ambient temperature).

The structure of other data packets, as they are stored in RAM 152 by MS controller 150 are also shown in FIG. 7. The ventilation (chest expansion sensor) packet vent-I consists of a single indicator bit followed by 23 bits of data in which are packed the timestamp relative to the last minute packet and the amplitude of the ventilation signal being reported. All quantities, except 4-byte timestamps in the minute packet, are stored most-significant-bit first ("big endian" as it is known in the art). Four-byte timestamps are stored in Intel byte-reversed format, though the bits in the individual bytes are stored byte-msb-first.

The EKG data in the present invention is stored using three separate compression/data reduction strategies. First, the raw EKG signal is converted into set of QRS description packets by the RT controller 148 which are then sent to the MS controller 150. Secondly, only the intervals between subsequent QRS events are stored in the RAM 152 for most heart beats, with the median values of the other features of the waveform being stored once a minute in the minute packet, as explained above. Finally, the QRS interval data itself is subjected to a significant degree of compression into one of three different types of EKG timing data packets which are distinctly different, and which are used depending on the amount of data compression which may be applied in a particular instance.

In FIG. 7, the longer two EKG data packets (EKG-ts and EKG-lid) each have a bit labeled "P" in their first byte. The "P" bit is a flag which is used during the decompression of EKG data to indicate the location of the next previous packet of EKG data. Because the EKG data is split into two separate zones of RAM 152, some of the packets may be EKG-sid packets which are located in EKG-sid zone 172, while others are EKG-ts and EKG-lid packets which are stored in the warehouse 170 (FIG.5). The "P" bit is set to a logical "1" in a particular EKG-ts or EKG-lid packet to indicate that there is at least one EKG-sid packet which immediately precedes it in time. Thus, as EKG data is being read out of the warehouse, if a packet is encountered for which the "P" bit is set to a logical "1", the decoding software jumps to the EKG-sid zone 172.

In the EKG-sid zone, EKG data is read out of memory until an "end-of-sequence" marker is encountered. Although the EKG-sid data packets are 8-bits each, with no indicator bits, an EKG-sid packet having the first bit set to a logical "1", and the next seven bits set to "0" (i.e. numeric value—128) is used as the "end-of-sequence" marker. This value is reserved, and no actual EKG-sid data is allowed to be stored with this value. Upon encountering this marker, the decoding software jumps back to the warehouse 170 to continue reading from the point at which the "P" bit was encountered.

As mentioned, the EKG-ts packet has four indicator bits, which are followed by twenty data bits. The EKG-lid packet has a three indicator bits, followed by thirteen data bits. Finally, the EKG-sid packet is simply a one-byte data packet, which is identified as being EKG-sid data simply by its storage in the EKG-sid zone. The selection of which packet type to use is based on the EKG compression algorithm and the irregularity of the EKG signal response. This may be better understood with reference to FIG. 8.

Figure 8:
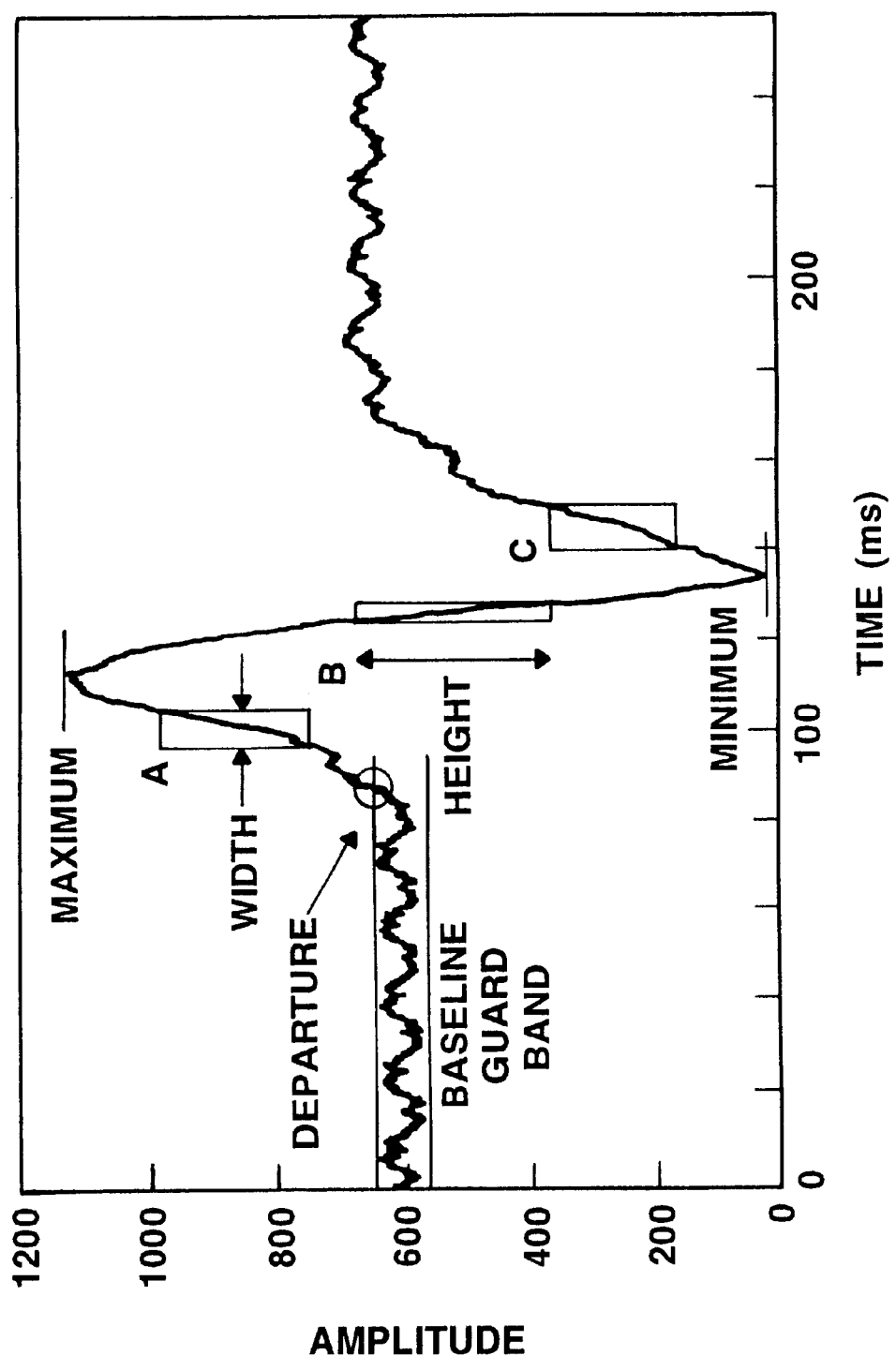
FIG. 8 is a graphical depiction of a EKG waveform demonstrating the EKG sampling points of the multiparametric monitor of the present invention.

FIG. 8 depicts a typical EKG signal pulse, as detected by the EKG sensor electrodes of the present invention. In order to minimize the data which is necessary to describe the waveform, the RT controller 148 collects only time event and feature measurement information for each signal pulse. Using its internal registers, the RT controller 148 retains information from a pulse which allows it to simplify the measurement of the next pulse. The feature measurements (labeled A, B, and C i n FIG. 8) are sent to the MS controller 150 for temporary storage in the scratchpad 168 portion of RAM 152 (FIG. 5). These measurements are collected over a period of one minute, and their median values are calculated and subsequently stored as part of the "minute" data packet in the warehouse 170 of RAM 152.

An EKG pulse as shown in FIG. 8 occurs each time the patient's heart muscle contracts and expands. The nature and cause of an electrical EKG signal is well known in the art and will not be discussed herein in any detail. Each pulse consists of a temporary increase in electrical potential caused by excitation of the patient's ventricles (i.e. depolarization), and is followed by a temporary decrease in electrical potential caused by recovery of the patient's ventricles (i.e. repolarization). In between pulses, the signal amplitude remains confirmed to a baseline level, the varying magnitude of which is primarily due to electrical noise or detected skeletal muscle signals.

To describe each EKG pulse, the present invention uses six different measurements: 1) the departure of the signal amplitude from baseline by more than a predetermined amount (which is selected to be at or near 10% of the prior pulse amplitude in this embodiment); 2) the slope of the initial increase in signal amplitude; 3) the maximum amplitude of the pulse; 4) the slope of the decrease from full positive amplitude to full negative amplitude; 5) the minimum amplitude of the pulse; and 6) the slope of the increase back to baseline from full minimum amplitude. The preferred method of obtaining this information involves the determination of time intervals between certain features of each waveform, from which the desired measurements can be approximated.

As mentioned previously, in the preferred embodiment, the EKG signal is sampled approximately 2500 times per second. An average EKG pulse is 80 ms long, which results in approximately 200 samples to describe each pulse. Certain features of each pulse are determined by the RT controller 148 from the samples, and used for making measurements in the next subsequent pulse. For one, the RT controller 148 maintains an average baseline value, which is continuously updated when the RT controller is not tracking an EKG pulse in progress. The RT controller also saves values derived from the maximum and minimum amplitudes of a current pulse which are used to assist in the detection of the feature points of the next pulse.

When a sample is received which indicates that the EKG signal has departed from the average baseline value by more than 10% of the amplitude of the prior pulse the RT controller enters into its QRS complex recognition routine. The subsequent data samples are then tested against values representative of 25% and 75% of the maximum amplitude of the previous pulse. The separation between these data samples in time is defined as the width (labeled as feature "A" on FIG. 8) of the depolarization up-slope, and this width value is measured and stored by RT controller 148. By knowing this width, an approximation of the median representative pulse up-slope may be generated. In the preferred embodiment, the width is saved by saving an indication of the time values for each of the 25% and 75% points (relative to the initial departure from baseline). The midpoint of feature "A" (50%) is considered the point of greatest slope and the four-byte absolute timestamp of this event is considered the "official" timestamp of the EKG.

The maximum value of the EKG pulse is determined by the RT controller 148 from the available samples, and is temporarily saved for use in finding the 25% and 75% points for the feature measurements in the next pulse. The next EKG measurement to follow the maximum value is the width of the down-slope from the maximum pulse value to the minimum pulse value (labeled as feature "B" in FIG. 8). This value is determined by using the maximum value and the minimum value from the next previous pulse as a measure of the peak amplitudes. The 25% points of each of these extrema are then found, and the collected data samples compared to them. The separation in time between 25% of the maximum and 25% of the minimum is indicative of the desired width measurement and so is measured and retained.

The minimum value of the pulse (like the maximum value) is temporarily saved for use in determining the 25% and 75% values for the feature measurements of the next pulse. The last measurement taken is the time between the 75% and 25% points of the repolarization upslope (labeled as feature "C" in FIG. 8). Like the previous measurements, this width uses the time separation between the 75% and 25% points of the minimum value stored from the previous EKG pulse. The time interval between these two points is measured and saved, along with the other saved time values, for transmission to the MS controller 150 and subsequent compression and long-term storage.

Because the expression of each of the absolute timestamps requires four bytes of memory, it is desirable to reduce this data size to allow for greater density of storage in RAM 152. Thus, instead of storing each of the timestamps, the intervals between successive timestamps are calculated for many of the EKG events. Because a regular interval between EKG events is expected, the data may be further compressed by calculating the difference between one interval and a subsequent interval.

In order to begin a calculation of interval differences, at least two consecutive timestamps must be known. Therefore, actual values of the first two timestamps are stored "as is" as EKG-ts data. The time interval between these two timestamps is then calculated. Upon the occurrence of a third event, the interval between the second and third events is calculated, and the second interval is subtracted from the first interval. The resulting value is the first calculable interval difference, and is stored as the third EKG data packet. Subsequent data packets are calculated and stored in the same manner (i.e. the third interval is subtracted from the second interval to find the second interval difference, the fourth interval is subtracted from the third interval to find the third interval difference, and so on).

Depending on the variation from one interval difference to the next, the interval differences may ultimately be stored in one of two different packet structures, the EKG-lid packet or the EKG-sid packet (see FIG. 7). Because a larger interval difference requires more space in memory, the selection of which packet structure to use is made based on the number of bits required to express the interval difference.

If the interval difference can be expressed in a maximum of eight bits, then it is stored by the MS controller 150 in the EKG-sid zone of RAM 152 in an "all-data" EKG-sid packet such as that shown in FIG. 7. If the interval difference requires more than eight bits, but fewer than fourteen bits, then it is stored by the MS controller 150 in the warehouse in the EKG-lid format shown in FIG. 7. Finally, if the interval difference requires more than thirteen bits to describe, the MS controller 150 stores an actual timestamp of the current EKG event relative to the last minute marker (as opposed to storing an interval difference). This timestamp is stored in the warehouse in the EKG-ts data packet format. Because the timestamp is relative to the last minute marker, four bytes are not necessary (as with the absolute timestamps stored with the minute packet). Instead, the data is stored in nineteen bits which fit in three bytes along with the encoding bits and the "P" bit.

Figure 9:
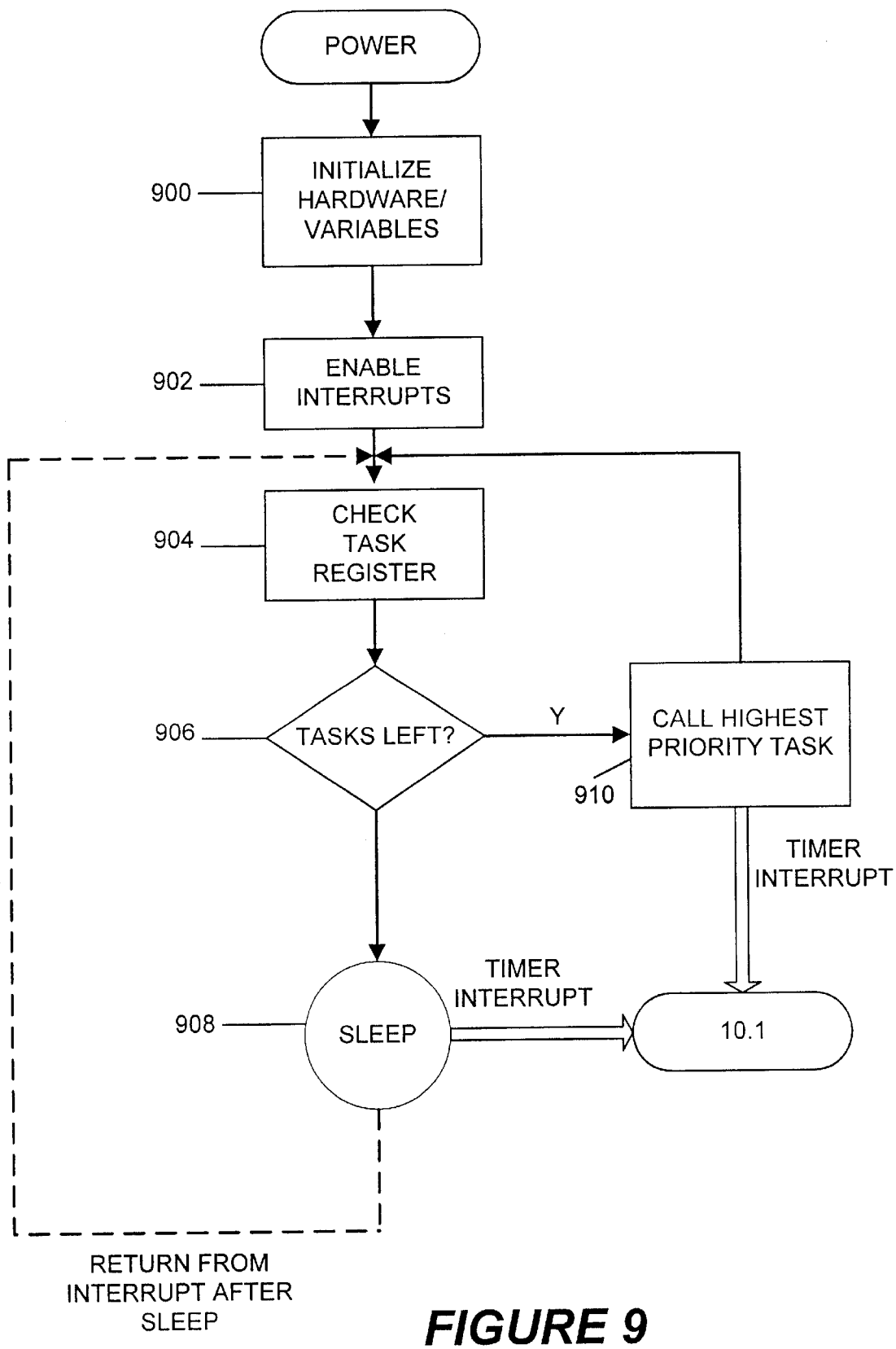
FIG. 9 is a flow chart depicting a software routine of a real time controller of the multiparametric monitor.

The logic flow of the firmware run by the RT controller 148 and the MS controller 150 is depicted in FIGS. 9–12. Referring to FIG. 9, when power is first provided to the RT controller 148, all registers and other memory of the controller are initialized at step 900. The controller is interrupt-driven, but it is only after initialization that the interrupts are enabled at step 902. The controller then examines an internal task register 904 which is used to store a list of pending controller tasks. Since the system has just been powered up, there are no pending tasks, and the controller proceeds from decision box 906 into a sleep state 908, where it waits for an interrupt message.

Figure 10:
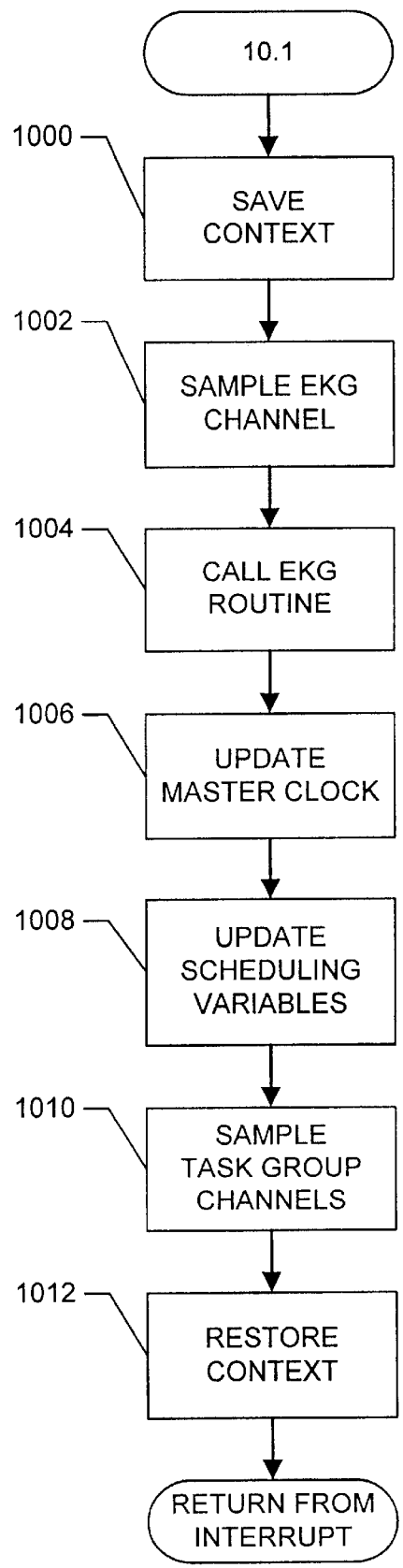
FIG. 10 is a flow chart depicting an interrupt routine of the real time controller.

The interrupt-generated process of the RT controller 148 is shown in FIG. 10. Each interrupt is generated by the 32.5 KHz crystal oscillator-based timer maintained by the hardware of the RT controller 148, the frequency of which is divided by 13 down to a 2.5 KHz interrupt cycle. Thus, in the preferred embodiment, one interrupt signal is generated each 400 $\mu$s. Each of the other service groups shown in FIG. 6 has a periodicity which is a multiple of the EKG period. The controller maintains a "master clock" which is incremented as part of the interrupt routine each time the interrupt signal is generated. Other counters are also maintained which trigger the activities for the other service groups every "nth" interrupt, where n is the multiple of the particular service group period in question relative to the interrupt signal period. Every service group, therefore, is ultimately driven by the same interrupt signal, thus ensuring timing accuracy and precision.

Referring to FIG. 10, when the timer-generated interrupt is received, the RT controller 148 suspends any processing activities already in progress. The existing context (i.e. contents of processor registers and variables) is saved in local memory at step 1000. The processor, in step 1002, then signals the ADC 146 to sample the EKG channel (i.e. to convert the analog signal present on the EKG input). The RT controller 148, in step 1004, then calls an EKG processing function which is shown in FIG. 11, and discussed in further detail below.

Once the EKG function is complete, the master clock is updated by the RT controller 148 in step 1006. The counters for the other service groups are decremented accordingly, and the scheduling for the other service groups is accomplished by setting the appropriate bits in a task register (step 1008). The task register is an eight-bit register which is maintained by the RT controller 148, where each of the lower four bits of the register is used to represent a task for a different service group. The 2.5 KHz group is never explicitly scheduled. When the bit for a particular service group is set to a logic "1", the RT controller 148 takes the data samples associated with that group. Subsequent processing tasks related to that data are performed at a later time, in between data collection cycles. When the processing of a task group is finished, the RT controller resets that group's task bit to logic "0", indicating completion. As shown in step 1010, all of the necessary samples for the non-EKG service groups having their task bit set to "1" are taken before any processing of those samples occurs. This is to prevent delays in the acquisition of samples while other processing activities are taking place, since such delays could skew the regularity of the sampling for some of the service groups.

After sampling is performed for the appropriate groups, the previously-stored context is reloaded into the appropriate registers (step 1012), and control is returned to the next instruction of the controller program after that during which it was interrupted. If the interruption came during the sleep cycle 908 of FIG. 9, control is returned to step 904 after processing the interrupt sequence of FIG. 10 (as shown by the broken line of FIG. 9). However, since the interrupt may also be serviced while the tasks are being processed in step 910, an interruption during this step causes a return to the next pending program instruction of the task processing of step 910.

In step 904 of FIG. 9, the task register is tested to see if there are any tasks pending. If so, the decision step 906 causes the highest priority task to be called. In the preferred embodiment, the priority of the tasks is according to the frequency of the related data sampling, with the higher sampling rate processing tasks having the higher priority. Since processing tasks may not yet be complete when the next interrupt cycle occurs, the processing must be suspended until the interrupt service is complete. Such postponements of the processing functions are problematic only if processing of a sample for a particular service group is not yet completed by the time the next sample for the same group is collected. Therefore, since the service groups with longer sampling periods have greater intervals between consecutive samples, they are assigned a lower priority to allow groups with shorter intervals to be serviced before them.

After the execution of a task in step 910 (which includes the resetting of the associated task bit), the task register is again checked in step 904. If further tasks are pending, step 906 again transfers control to step 910, where the (now) highest priority task is executed. This process continues until no tasks remain, at which time step 906 causes the RT controller 148 to enter sleep state 908.

The processing of EKG samples -performed by the RT controller 148 is demonstrated by the flow chart of FIGS. 11A–11D. This processing is adaptive in that it responds to the changes in the sampled data itself. In order to reduce the amount of stored EKG data, only samples which are taken during an EKG pulse are used for calculating the stored EKG data. As discussed previously with regard to FIG. 8, the only EKG data which is ultimately stored in RAM 152 are the feature measurements and the interval information between individual EKG events. Preprocessing for this data compression is performed by the RT controller 148 via the program flow shown in FIGS. 11A–11D.

As shown in step 1100, with each new EKG sample, the RT processor updates a running average sample value indicative of the baseline value of the EKG signal. Each new sample is also tested against the baseline in step 1102 to determine whether it has exceeded the baseline average by more than a predetermined amount. In the preferred embodiment, the predetermined amount is equal to 10% of the baseline average, and represents a "guard band" which reduces false determinations of the initial upslope of an EKG pulse. As shown in step 1102, each sample value is tested to determine whether it exceeds the sum of the baseline and the guard band and, if not, control is returned to step 1100.

If the baseline/guard band total is exceeded, the RT controller proceeds to step 1104, where the sample value is compared to the value 0.25 $Y_{MAX}$ where $Y_{MAX}$ is the stored maximum value from the previous sample. Each successive sample is tested against this value until it is exceeded, whereupon a sample counter is started. For each successive sample, the sample value is first tested against the value 0.5 $Y_{MAX}$ in step 1105 and, for each sample which does not exceed this value, the sample count is incremented in step 1109. When the 0.5 $Y_{MAX}$ value is exceeded, the timestamp for the current EKG pulse is recorded in a temporary memory location in step 1107. The program flow then proceeds to step 1108, where the sample value is repeatedly tested against the value 0.75 $Y_{MAX}$. For each subsequent sample which does not exceed the 0.75 $Y_{MAX}$ test value, a sample counter is incremented in step 1110. Once the 0.75 $Y_{MAX}$ value is exceeded, the sample count is stored in step 1112 to a temporary memory location as SCOUNTA. This and all EKG measurements are stored in memory on the RT controller 148 itself in a format which facilitates efficient transmission to the MS controller 150.

In the next stage of the sample processing, the sample value is tested to determine whether it is a maximum point of the EKG pulse. This is accomplished in the flow logic of FIG. 11A by the comparison of the current sample value "s[n]" to a previous sample value (s[n−1]) minus a constant Δ. Δ is a predetermined tolerance which ensures that the sample value is changing by an amount sufficient to differentiate between noise and an actual change in signal direction. As the EKG signal rises, the value P (initially set in step 1109 to the first value of S after storing SCOUNTA) is updated each time the EKG value is greater than P+Δ (steps 1114 and 1115, FIG. 11B). If the signal should happen to fall slightly, but not as far as P−Δ, it is construed as noise, P is not updated, and no other changes are made. Only when the signal falls below P−Δ (as tested in step 1116) has it been "firmly" established that the signal has begun its downslope. At that point (step 1117), the most recent value of P is declared the maximum point of the EKG signal, and is stored as $Y_{MAX}$ to be used for the processing of the next EKG pulse. If the overall EKG signal is rejected at some point in the EKG routine, it is determined that a valid EKG event did not occur, and the old $Y_{MAX}$ and $Y_{MIN}$ values are retained for use in processing the next pulse.

Figure 11A:
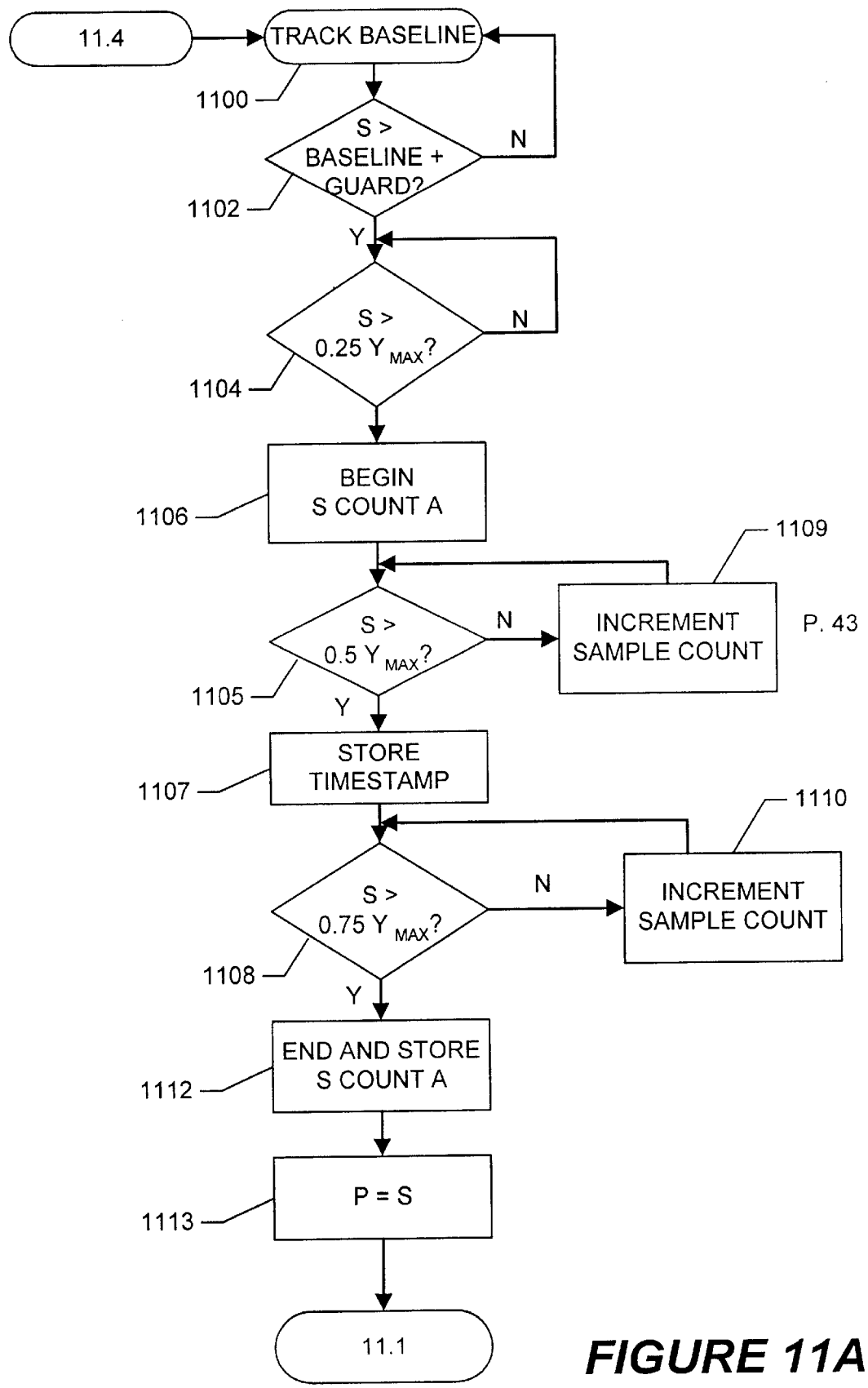
FIGS. 11A–11D together make up a flow chart depicting an EKG signal processing routine of the real-time controller.
Figure 11B:
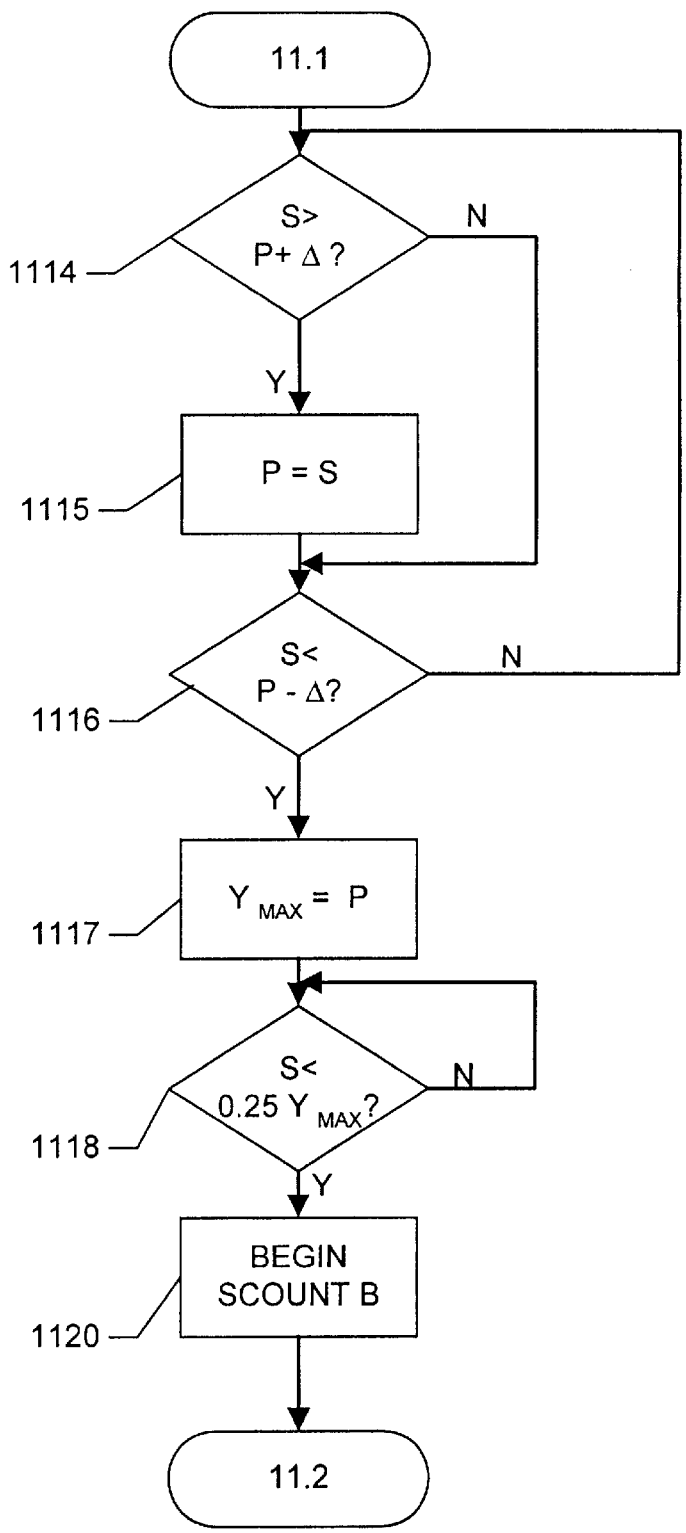
Figure 11C:
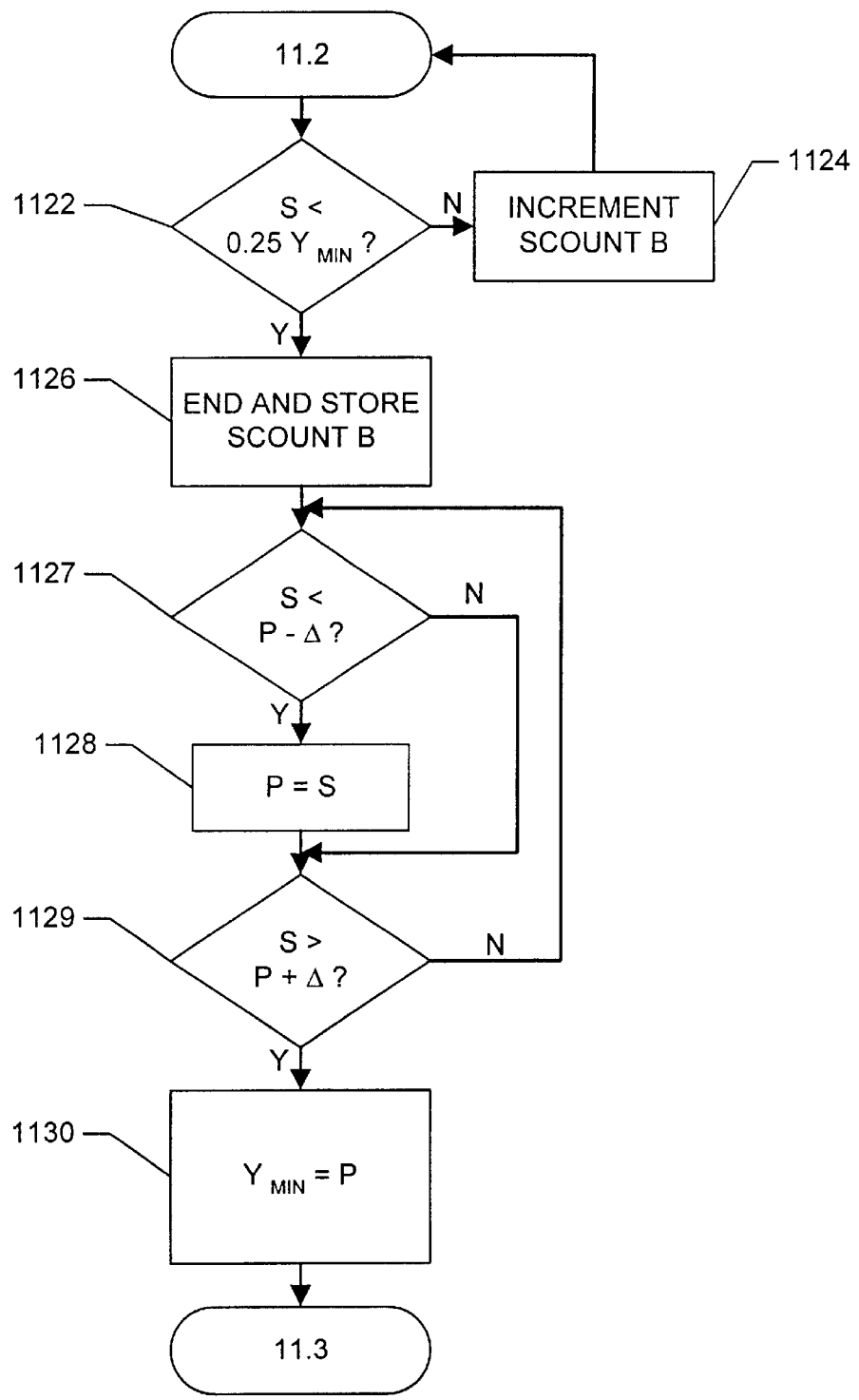
Figure 11D:
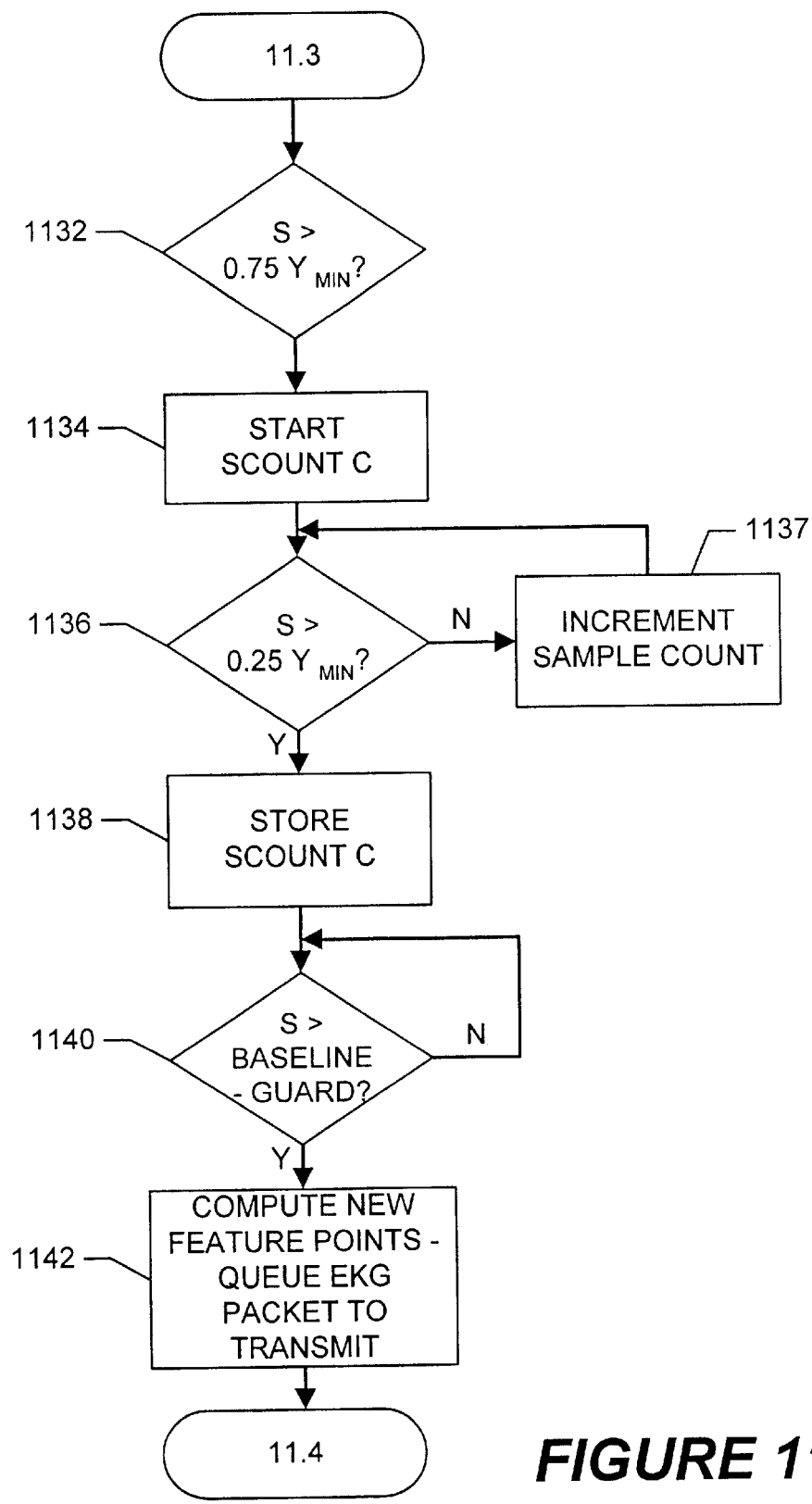

The next data collection stage is for the width of the down slope. In step 1118, the sample value is compared to the value 0.25 $Y_{MAX}$. The RT controller 148 cycles through step 1118 with each sample until a sample is encountered which is less than the 0.25 $Y_{MAX}$ value. At that time, a sample counter SCOUNTB is started in step 1120. Referring to FIG. 11C, the RT controller 148 begins comparing subsequent samples to the value 0.25 $Y_{MIN}$ in step 1122, where YMIN equals the minimum sample value stored during the next previous EKG pulse. For each sample which is not less than 0.25 $Y_{MIN}$, the sample counter is incremented in step 1124. Once a sample less than 0.25 $Y_{MIN}$ is encountered, the total of the sample count is stored in step 1126.

The determination of $Y_{MIN}$ value is similar to the determination of $Y_{MAX}$, changed as needed to detect the first rise from a falling signal instead of the first fall from a rising signal. In steps 1127 and 1128, the sample value is repeatedly tested against the value P−Δ, and the value of S replaces P when it is more than Δ less than P. This ensures that P will be a true minimum (excluding noise fluctuations within the Δ error range). In step 1129, the sample value "S" is tested against P+Δ and, if it exceeds P+Δ, P is stored as $Y_{MIN}$ in step 1130. Because the increase in the sample value above P+Δ indicates the beginning of an upslope, $Y_{MIN}$ is thus a valid determination of the minimum point on the EKG curve.

After the minimum value is determined, the RT controller 148 begins comparing the samples to the value 0.75 $Y_{MIN}$ in step 1132 (FIG. 11). Once this value is exceeded, a sample counter is started in step 1134. The RT controller 148 then begins testing samples against the value 0.25 $Y_{MIN}$ in step 1136, and, in step 1137, increments the sample counter once for each sample which does not exceed the 0.25 $Y_{MIN}$ value. Once 0.25 $Y_{MIN}$ is exceeded, the RT controller 148, in step 1138, stores the accumulated sample count as SCOUNTC.

After step 1138, the RT controller 148 begins comparing the sample values to the value of the baseline average minus the guard band value (step 1140). Once a sample is encountered which has a value within 10% of the baseline, the RT controller 148 determines that a valid EKG event has been detected and advances to step 1142. The RT controller then computes the new "feature points," which are the values of $0.25\,Y_{MAX}$, $0.75\,Y_{MAX}$, $0.25\,Y_{MIN}$ and $0.75\,Y_{MIN}$ which are found using the newly-measured extrema, and which will be used during the processing of the next EKG pulse samples. In this step, the RT controller 148 also assembles the EKG packet using the newly acquired data and queues it up for transmission to the MS controller 150. The RT controller then returns to step 1100 for the next EKG sample (FIG. 11A) to continue updating the baseline average.

During each of the steps of the program depicted in FIGS. 11A–11D in which new samples are detected, a timer is initiated (or reinitiated) which, when it expires, causes the processing of the samples for the current pulse to cease. This timer provides an upper limit on the waiting period for certain sample values to be acquired. By reinitializing the timer with each step, the same amount of time is provided for each to advance to the next step. If the timer expires during any of these steps, the RT controller 148 proceeds to a wait state where it stays until the EKG signal returns to within the baseline guard band. Due to the timer expiration, the signal is determined to be an invalid QRS complex, and no data is transmitted to the MS controller and no new feature points are computed. Once the EKG signal has resumed, the RT controller 148 returns to step 1100 where it continues to track the baseline average.

The processing of each ventilation sample begins when the RT controller 148 comes across the ventilation task bit set in the task register, and responds by instructing the ADC 146 to convert a sample from the chest expansion sensor channel. The converted signal is then received by the RT controller 148 for processing.

Figure 12A:
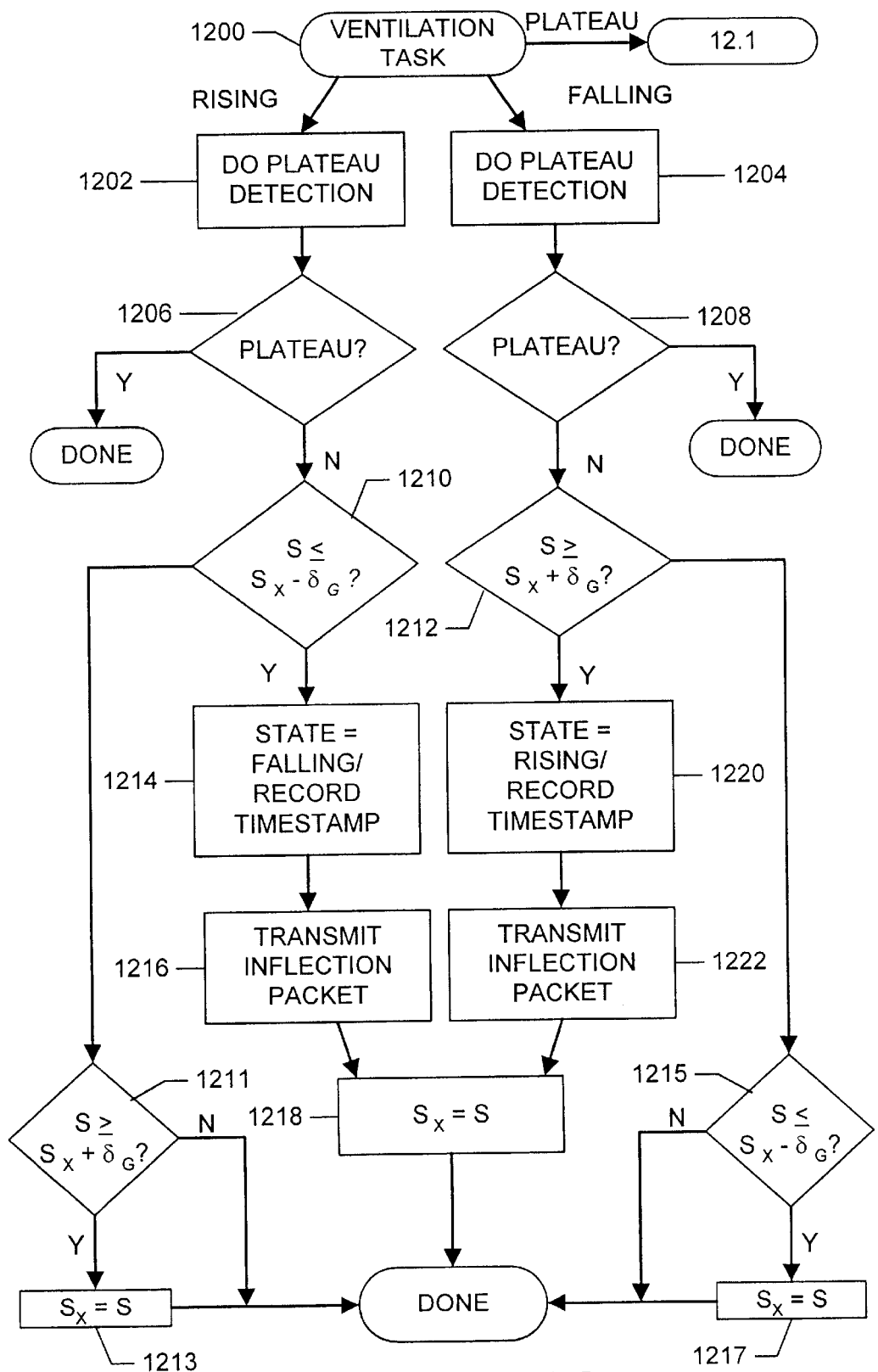
FIGS. 12A and 12B depict a flow chart of a ventilation signal processing routine of the real time controller.
Figure 12B:
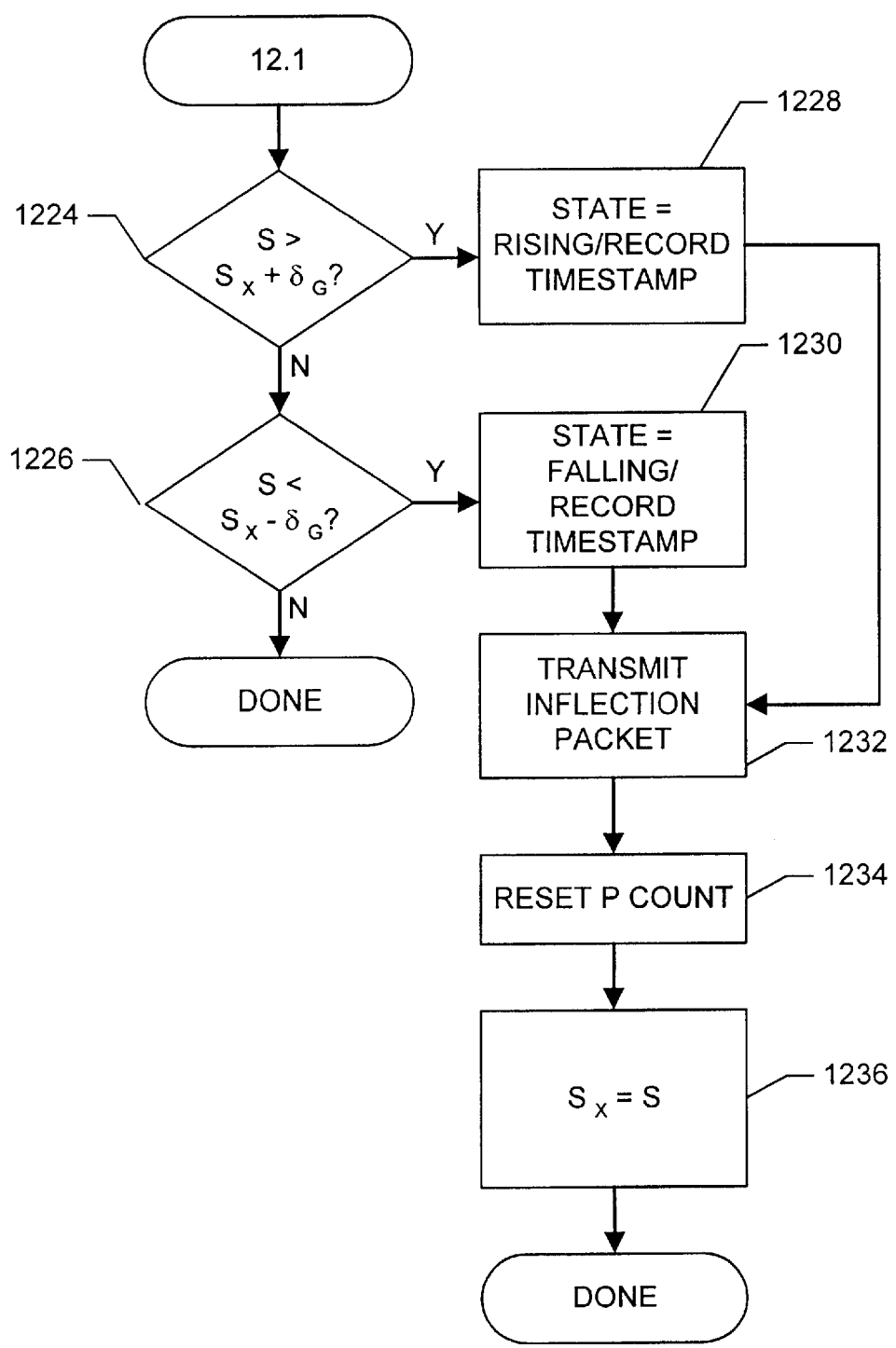

FIGS. 12A and 12B depict the ventilation processing routine of the RT controller 148. As shown, when the task begins (in state 1200), the controller can follow one of three different paths, depending on the value stored in a "state" register of the RT controller 148. Different values in the state register are used to indicate the current state of chest expansion as being "rising", "falling" or "plateau." A value indicating a "rising" state is stored in the state register when the patient's chest circumference was larger in the last sample, relative to the sample before it, by a predetermined amount. Similarly, a value indicating a "falling" state is stored in the state register when the patient's chest circumference was smaller in the last sample, relative to the sample before it, by a predetermined amount. Finally, a value indicating a "plateau" state is placed in the state register when the patient's chest has neither expanded nor contracted by at least the predetermined amount over a set number of consecutive samples.

The path in the ventilation routine which the RT controller 148 takes when the task is begun is determined by the current value in the state register. These different paths have been identified in FIG. 12A by the conditions which the values in the state register represent (i.e. rising, falling or plateau). A ventilation packet is transmitted only when it indicates an "inflection point" (the start of a "rising" or "falling" chest expansion period), or the start of a "plateau" condition (when the state of the patient's respiration does not change for a predetermined time). Each ventilation packet transmitted to the MS controller 150 contains a timestamp of the sample and the digital value of the sample. This data is then converted into the vent-I packet structure discussed previously with regard to FIG. 7.

Each of the rising and falling paths of the FIG. 12A flow chart begin by calling a plateau detection function in steps 1202 and 1204, respectively. The plateau detection function keeps track of the number of consecutive samples for which the ventilation signal remains substantially unchanged as a measure of whether a "plateau" in the patient's respiration has been reached. This function is demonstrated by the flow chart of FIG. 13.

Figure 13:
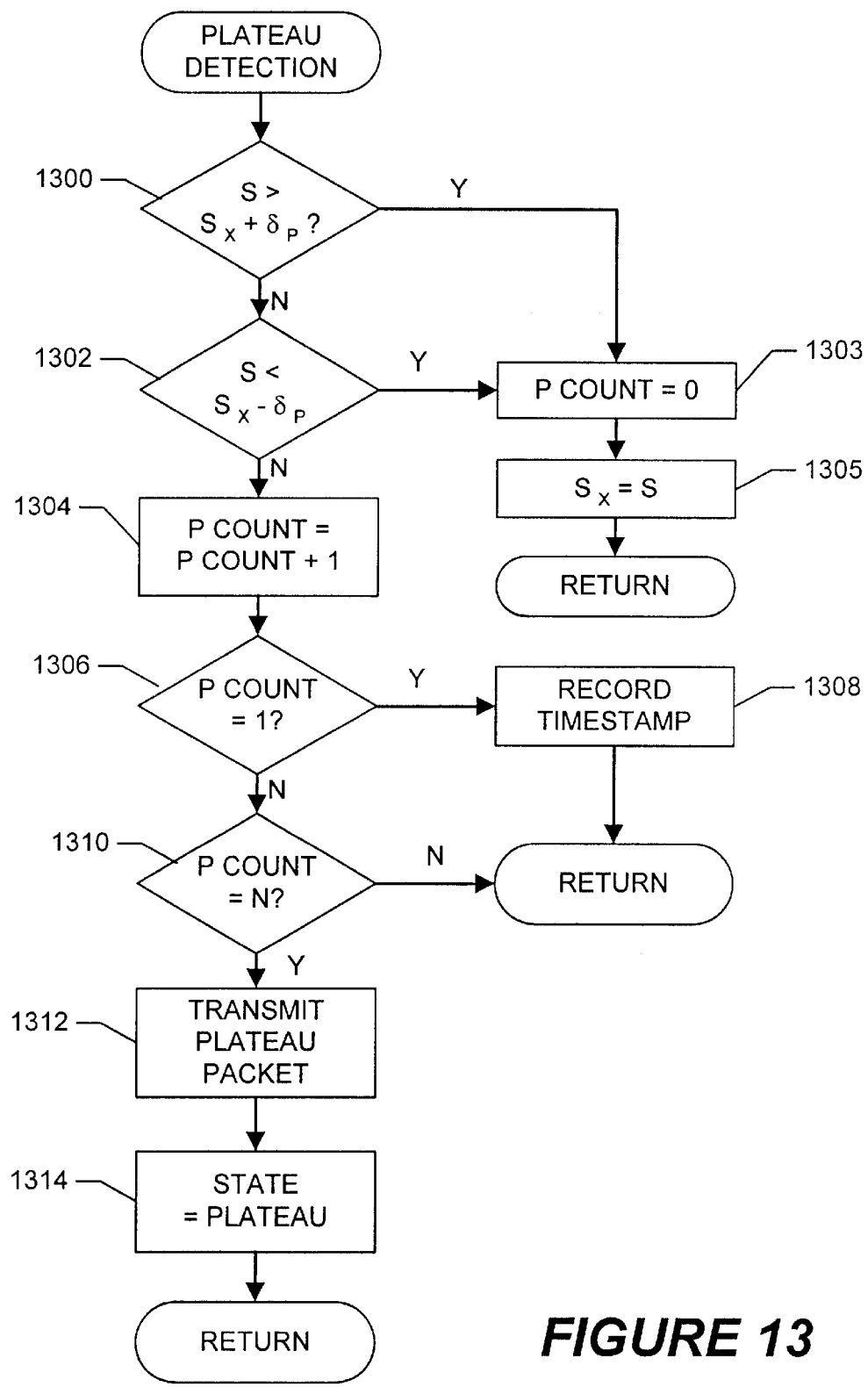
FIG. 13 is a flow chart depicting a plateau detection function used during the ventilation signal processing routine of the real time controller.

As shown in FIG. 13, the value of the present sample ("S") is first compared to the value $S_X$. $S_X$ is a temporary variable in which the value of a previous sample is stored, and which provides a reference value against which to test for deviation from a predetermined guard band (either plateau guard band $\pm\delta_P$, or rising/falling guard band $\pm\delta_G$). In step 1300, the sample is first tested to determine whether it exceeds the value of $S_X+\delta_P$, where $\delta_P$ defines a plateau guard band and represents a limit beyond which the sample value must deviate from $S_X$ to be considered a state change during the plateau detection function. Similarly, S is tested against the other side of the plateau guard band (i.e. $S_X-\delta_P$) in step 1302. In either case, if the sample value has deviated by more than $\delta_P$ since the last state change, the value of variable PCOUNT is set to zero in step 1303, $S_X$ is set to the value of the current sample in step 1305 and the plateau detection function is terminated, with control being returned to step 1206 or step 1208 of FIG. 12A, as appropriate.

If the sample value is within the plateau guard band, the value of a plateau counter PCOUNT is incremented in step 1304. If the value of PCOUNT is equal to one (step 1306), indicating that the current sample is the first sample of a potential plateau, the timestamp of the sample is recorded in step 1308 as an indication of when the current plateau measurement began. Control is then returned to the appropriate step (i.e. 1206 or 1208) of FIG. 12A. If PCOUNT is not equal to one, it is tested in step 1310 to determine if the count has reached "N", which is the count value for which a plateau will be declared. In the preferred embodiment N equals 30, but those skilled in the art will recognize that other values may alternatively be used. If PCOUNT is found to not yet equal N in step 1310, control is returned to either step 1206 or 1208 of FIG. 12A, as appropriate.

If PCOUNT is found to equal N in step 1310, a plateau is confirmed, and a plateau packet, including the timestamp stored in step 1308, is transmitted to the MS controller 150 in step 1312. The state variable is then set to indicate a plateau state in step 1314, and control is returned to step 1206 or 1208 of FIG. 12A, as appropriate.

Referring again to FIG. 12A, when the plateau detection function, called in either step 1202 or 1204, is complete, the state variable is tested in either step 1206 or 1208, as appropriate, to determine whether a plateau has been found (i.e. if the state register has the "plateau" value stored in it). If so, the RT controller 148 exits the ventilation routine. If no plateau has been found, the program advances to determine whether a rising or falling state change has occurred.

On the "rising" flow path, step 1210 tests the sample value against a lower guard band limit which is defined by $S_X-\delta_G$, where $\delta_G$ is the limit beyond which a sample value must deviate from $S_X$ to be considered a state change while on the "rising" or "falling" flow paths. If the sample is found in step 1210 to be above the lower guard band limit, then the rising condition is unchanged. The sample value is then tested in step 1211 against an upper guard band limit defined by $S_X+\delta_G$ to determine whether it is necessary to update the value of $S_X$. If the sample value does not exceed the upper limit, the routine exits. However, if the patient's chest has expanded beyond the upper guard band limit, then the value of $S_X$ is set to the current sample value in step 1213 to ensure the accuracy of subsequent guard band tests, after which the routine exits. If, in step 1210, the sample value is found to be below the lower guard band limit, the state variable is changed to falling in step 1214, an inflection packet (including the current timestamp) is transmitted to MS controller 150 in step 1216 and the sample value is stored as the value for $S_X$ in step 1218, after which the routine exits.

The "falling" flow path functions in an essentially symmetrical manner to the "rising" path in that, if the sample value in step 1212 is found to be below the upper guard band limit, then the state variable is not changed, and the routine exits if the sample is not found to be outside the lower guard band limit in step 1215. If the sample is found to be outside the lower guard band limit in step 1215, the current sample value is stored as $S_X$ in step 1217, after which the routine exits. However, if the sample value is above the upper limit of $S_X+\delta_G$, in step 1212, then the state variable is set to rising in step 1220, an inflection packet is transmitted in step 1222 (including the current timestamp) and the sample value is stored as the new value for $S_X$ in step 1218, after which the ventilation routine exits.

The third branch of the flow chart is the "plateau" branch is depicted in FIG. 12B. This path is followed by the RT controller 148 during the processing of a sample when the state variable indicates that a plateau has been declared. In step 1224, the RT controller 148 first tests the sample value against the upper guard band limit $\delta_G$. If the sample value is not above the upper guard band limit, then it is then tested against the lower guard band limit $S_X-\delta_G$ in step 1226. If the sample value is not below the lower limit, then the plateau condition continues, and the routine exits.

If the sample value is found to be above the upper guard limit $S_X+\delta_G$ in step 1224, the state register is set to "rising" and the current timestamp is recorded (step 1228). Similarly, if the sample is found to be below the lower guard limit in step 1226, the state register is set to "falling" and the current timestamp is recorded (step 1230). Each of steps 1228 and 1230 is followed by the transmission of an inflection packet to the MS controller 150 in step 1232. The plateau counter PCOUNT is then reset in step 1234, the current sample value is stored as the new value of $S_X$ in step 1236, and the routine exits.

Figure 14:
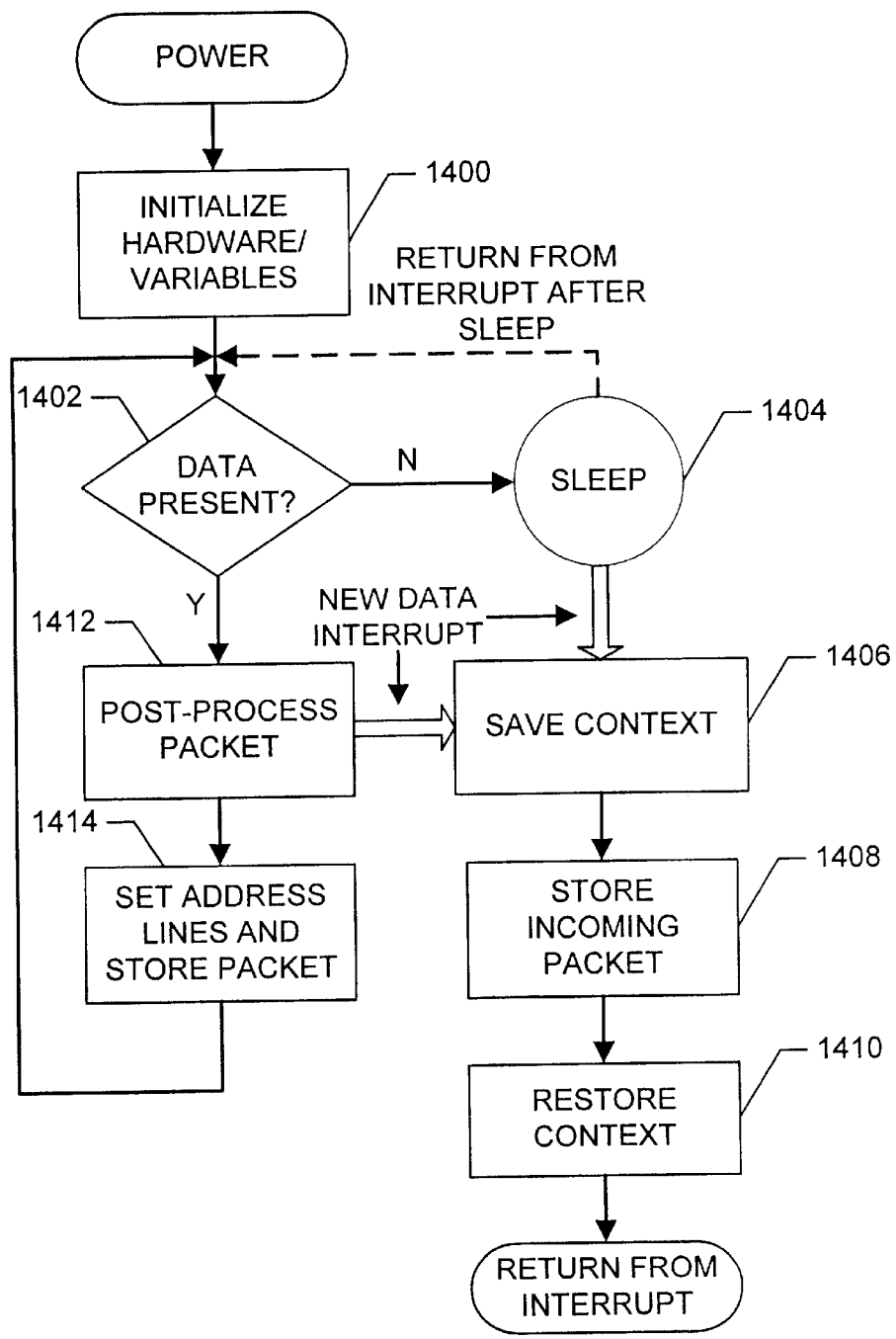
FIG. 14 is a flow chart depicting a software routine of a memory server controller of the multiparametric monitor.

FIG. 14 is a flow chart depicting the processing steps of the MS controller 150. When initially powered, the MS controller hardware and variables are initialized in step 1400. The MS controller 150 then checks for data present in the scratchpad of RAM 152 in step 1402 and, if no data is present, enters a sleep state 1404, in which most of the MS controller's circuits are powered down, except those which monitor for the "wakeup" (i.e. new data interrupt) signal from the RT controller 148.

If there is data present in step 1402, then the MS controller 150 proceeds from step 1402 to step 1412 where it performs the necessary post-processing tasks (i.e. data compression and/or packet assembly) on the oldest data packet stored in the scratchpad). During the post-processing of step 1412, the MS controller 150 may be subject to the new data interrupt from the "wakeup" signal. After post-processing, the MS controller proceeds to step 1414, where it sets the appropriate address lines of RAM 152 and stores the processed data. The program continues at step 1402 to check the data queue for more data.

The data interrupt causes the MS controller 150, whether in step 1412 or in sleep state 1404, to proceed to step 1406, where the current context of the controller is saved. The MS controller then services the "wakeup" request of the RT controller 148 by storing the incoming data packet in some of its working memory space (i.e. the "scratchpad") of RAM 152 in step 1408. This interrupt feature ensures that the operations of the RT controller 148 (which are more time-critical than that of the MS controller 150) are not delayed by the data processing and storage operations of the MS controller 150. The context is then restored in step 1410, and the MS controller proceeds to the next instruction step after the one during which it was interrupted. In the case of an interrupt during sleep state 1404, this next instruction is to proceed to step 1402 to check for new data in the data queue (as shown by the broken line of FIG. 14). If the interrupt request came during step 1412, the controller resumes its data processing tasks in step 1412 wherever it left off.

SUBJECTIVE DATA LOGGER

Figure 15:
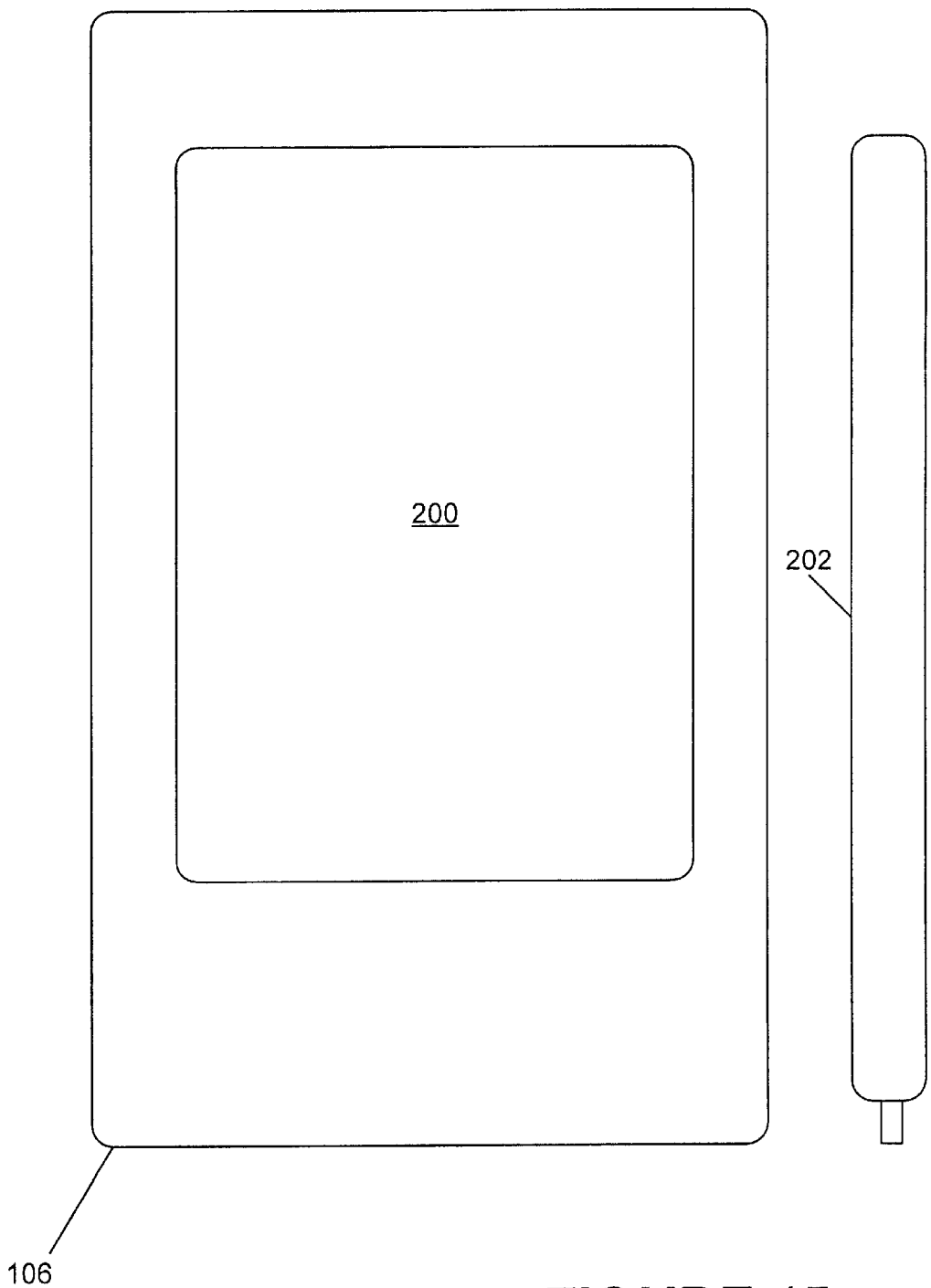
FIG. 15 is a front view of a subjective data logger of the present invention.

The subjective data logger 106 of the present invention may take the form of any data input device, including a personal computer. However, because it is desirable to provide the patient with a portable data logger which will allow the patient to record events at any time during the day, the present invention makes use of a battery-powered, handheld data input device such as the Newton® Message Pad, a registered trademark of the Apple Computer Corporation. Such a device is shown in FIG. 15, and includes a liquid crystal display (LCD) screen 200 which is interactive in that a patient may use a stylus or "pen" 202 to provide inputs to the data logger 106 by touching the pen 202 to the screen 200. The data logger 106 has a continuously running clock such that, when there is a data entry by the patient, the time of the entry is automatically recorded to provide a timestamp such as that used with the multiparametric monitor 108. Time is synchronized between the database, the monitor, and all other entities involved with collection and storage of data each time a data connection between these components is established.

Because methods of programming the Newton® Message Pad are well-known in the art, the specific program steps for the data logger 106 are omitted from this description. The data logger 106 is described, instead, in terms of its screen displays and available inputs and outputs. Those skilled in the art will recognize that there are a number of known ways to program these features into the data logger 106, and that it is the specifics of the type of data collected and the interactive features of the data logger which are particular to the present invention.

Figure 16A:
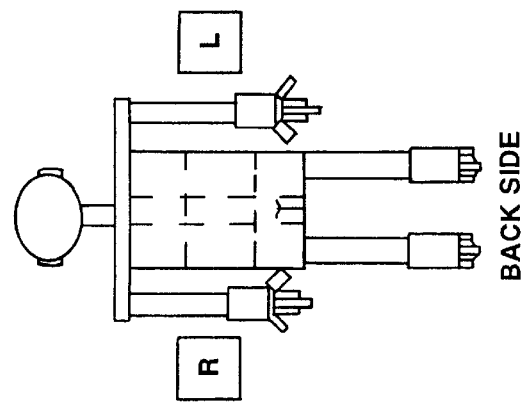
FIG. 16A depicts a "pain location" screen display of the subjective data logger on which a front view of a human body is shown.
Figure 16:
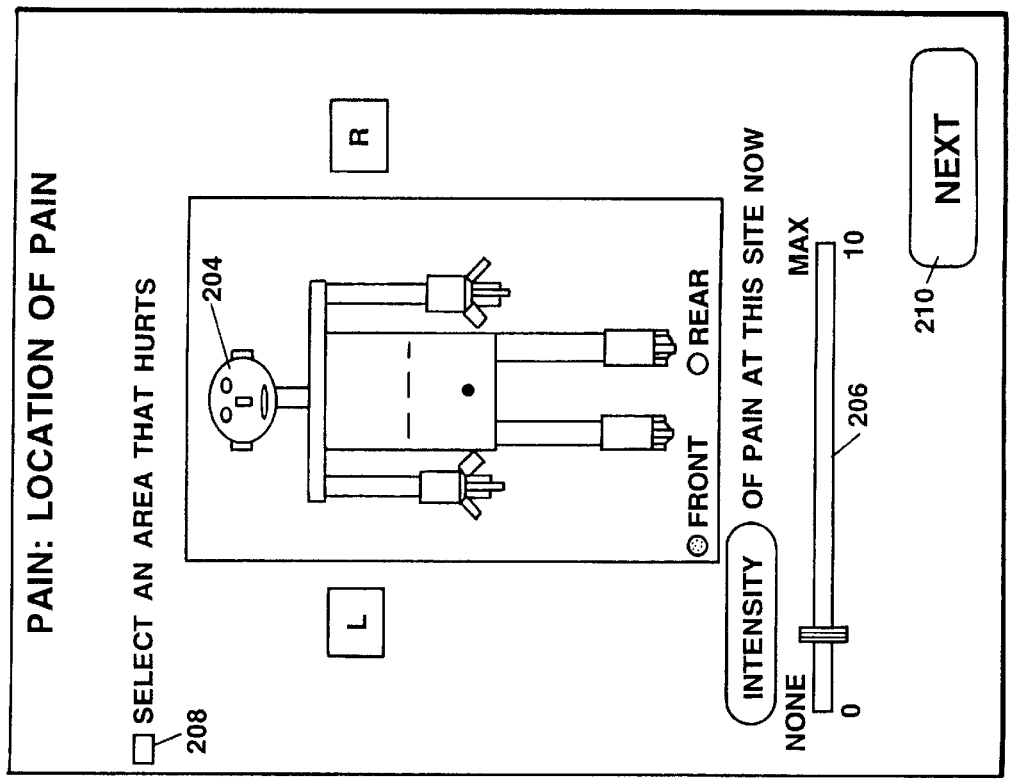
FIG. 16 depicts a "pain location" screen display of the subjective data logger on which a magnified view of a particular portion of a human body is shown.

Some of the input methods provided with the data logger 106 of the present invention are demonstrated by FIGS. 16–20, which show several of the screen displays of the preferred embodiment. FIG. 16 shows a "pain location" screen by which the patient may log the location and severity of pain which they experience. As depicted in the figure, the screen display includes an image of a human body 204 and a sliding input scale 206 for indicating the intensity of the pain. The screen display of FIG. 16 includes a prompt to the patient for inputting data, as demonstrated by prompting message 208, which requests that the patient indicate an area of the body which hurts.

Data selections are made by the patient touching the pen 202 to a portion of the display 204 of the human body which corresponds to a location of pain on their own body. The patient then touches the pen 202 to a part of the sliding scale 206 to indicate the relative severity of their pain. When the "next" region 210 of the screen is touched with the pen 202, the selected region of the body and the intensity value are recorded, along with the current timestamp, and the subjective data program advances to the next input screen.

Also located on the screen of FIG. 16 are regions 212, 214 of the screen for selecting either a front view or a rear view of the human body image 204. The front view is depicted in FIG. 16, and an isolated view of the body image which is displayed when a rear view is selected is shown in FIG. 16A. The use of two different views allows the patient to be more specific when indicating the location of the experienced pain. As with each of the data input displays, the display of FIG. 16 includes prompts to the patient for the data to be input. A prompting message 208 requests that the patient indicate an area of the body which hurts.

Figure 16B:
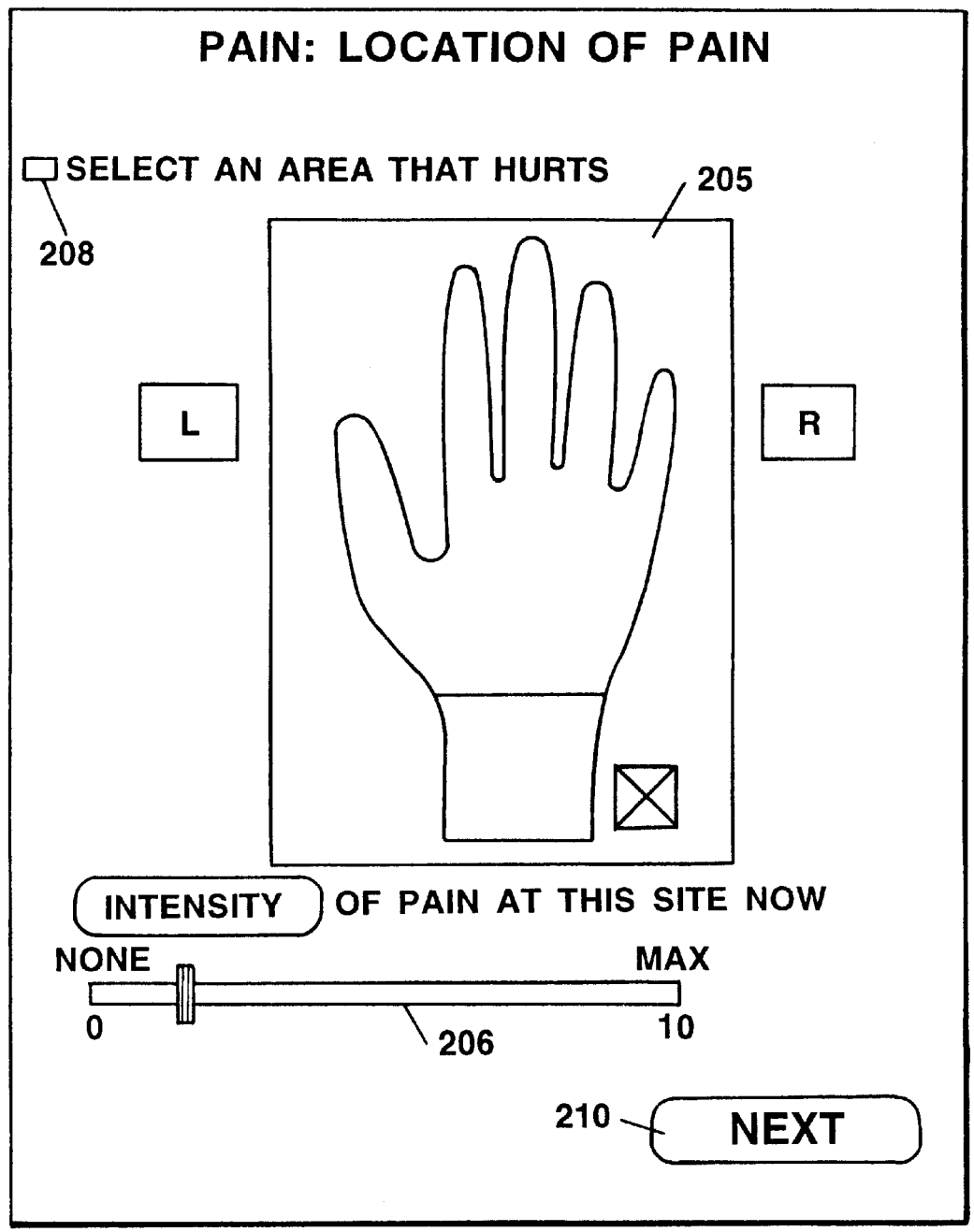
FIG. 16B depicts a "pain location" screen display of the subjective data logger on which a rear view of a human body is shown.

In one embodiment of the invention, the selection of certain portions of the body image on the screen of FIG. 16 by the patient touching those portions with the pen results in a new screen being displayed which contains a magnified image of the selected area of the body. For example, in FIG. 16B, the image of a human hand 205 is displayed in response to the user selecting the hand region of the main body image 204 of FIG. 16. This magnified image may then be used by the patient to select a portion of the body more specifically (e.g. one of the fingers of the hand). As with the main screen of FIG. 16, the sliding scale 206 and the prompting message 208 are displayed for the user. Selection of the "next" region 210 in the magnified body part screen causes the data logger program to advance to the a pain history screen, as discussed below.

Figure 17:
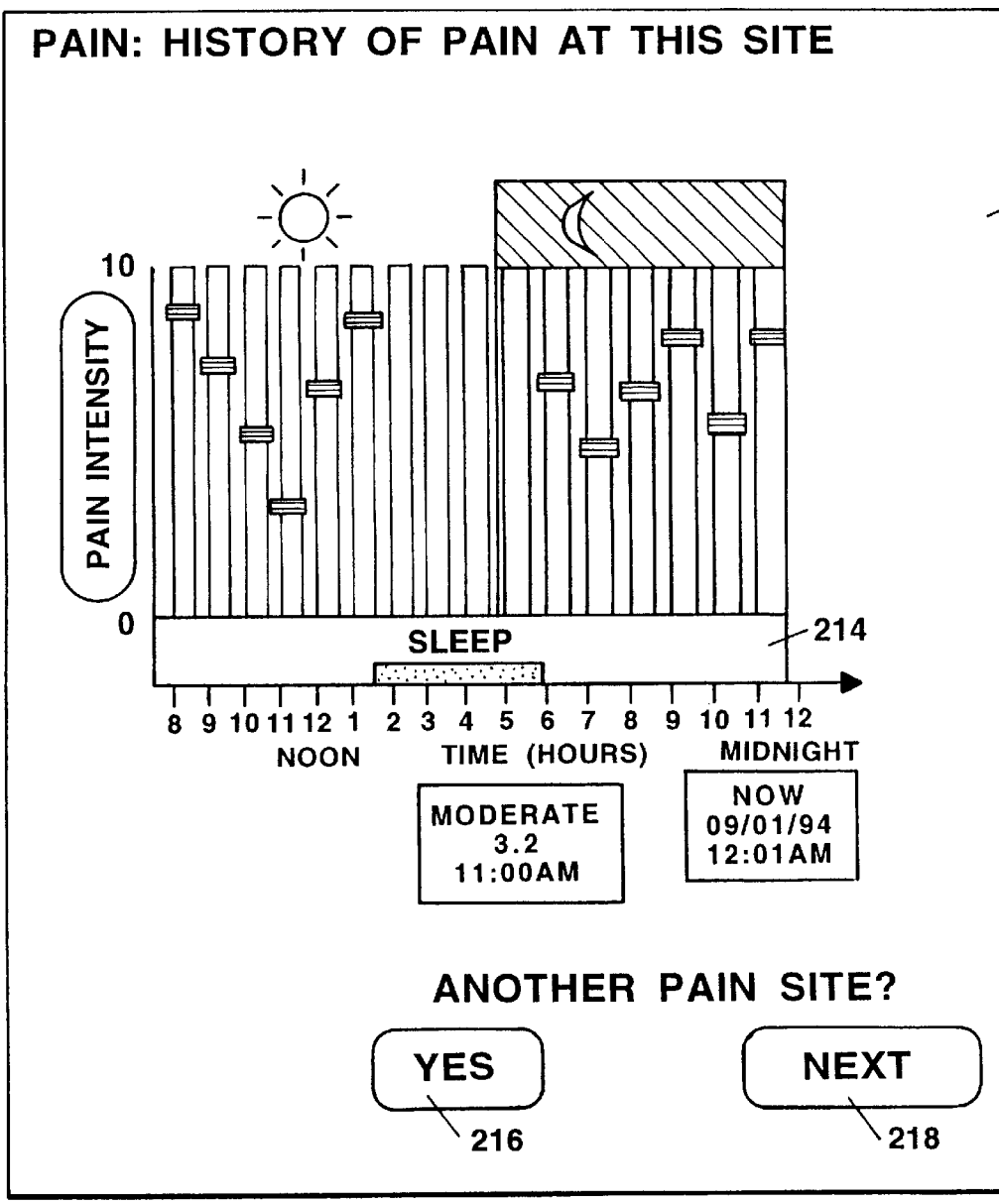
FIG. 17 depicts a "pain history" screen display of the subjective data logger.

After selecting the "next" region 210 of the pain location screen (either the main screen of FIG. 16 or the magnified image screen of FIG. 16B), the preferred embodiment of the data logger 106 advances to a pain history screen 212 with which the patient can indicate the recent history of pain in that particular region. This screen is depicted in FIG. 17, and allows the patient to input the pain history in a graphical format. The graph displayed has a sliding intensity scale along the vertical axis, and a time scale along the horizontal axis. By touching the pen 202 to a particular region of the graph, the patient can indicate a level of pain intensity at a particular time of day. A sleep scale 214 is also provided, and is aligned with the time scale of the horizontal axis of the history graph. This sleep scale 214 allows the patient, by touching the pen 202 to different regions of the scale, to indicate the time of day during which he or she was asleep.

Once the patient has made selections indicating a pain history and has entered any appropriate sleep data, the "yes" region 216 of the screen may be selected with pen 202 in response to the prompt as to whether the patient wishes to document another pain site. If "yes" is selected, then the current data selected on the screen 212 is recorded, along with a current timestamp, and a new pain location screen (as shown in FIG. 16) is displayed. If the patient wishes to move on to another type of subjective data input, the "next" region 218 may be selected. This results in the storage of the selected data and the timestamp, and advances the subjective data program to a new data screen.

Figure 18:
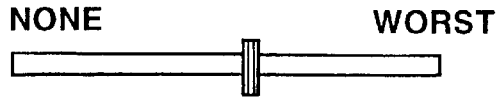
FIG. 18 depicts a "mood" screen display of the subjective data logger.

Another of the subjective data input screens of the preferred embodiment is the "mood" screen 220 shown in FIG. 18. The "mood" screen allows the patient to input his or her relative level of different emotions. Several of these are depicted on the screen 220 of FIG. 18, and those skilled in the art will recognize that many more similar mood or emotion categories may be included. Those displayed on the screen 220 are depression, anxiety and irritability. The sliding scales adjacent to each of the labels for these emotions allow the patient to select the relative severity of the emotion in question. Once the selections have been made, the patient selects the "next" region 222 of the screen with pen 202, and the subjective data program advances to the next screen.

Figure 19:
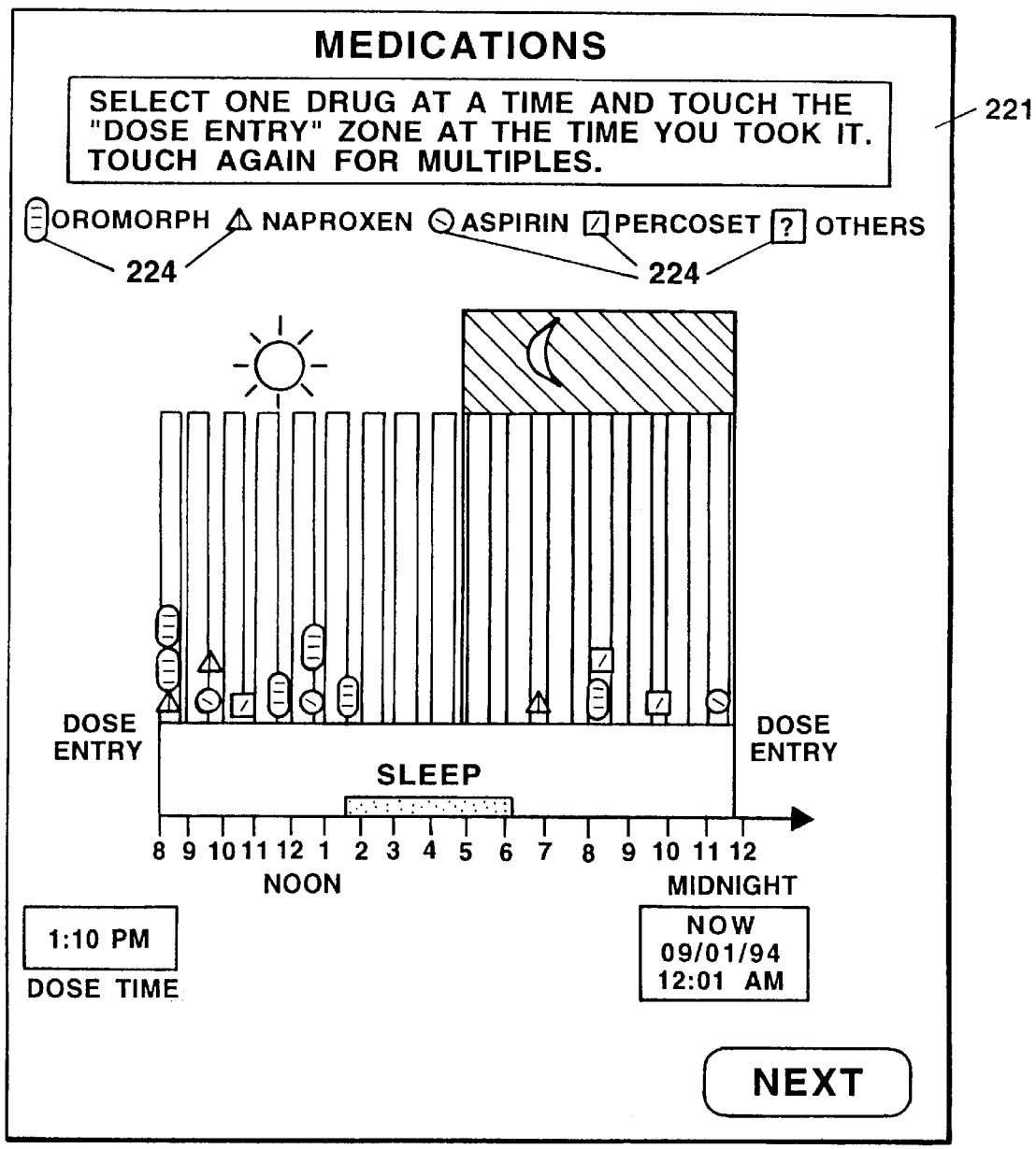
FIG. 19 depicts a "medication history" screen display of the subjective data logger.

FIG. 19 is a display screen 221 which is in the form of a medication timeline. The horizontal scale shows relative times of day, and by selecting one of the drugs indicated by the drug regions 224 of the screen and then selecting a particular time of day, the patient may record that one dose of that particular drug was taken at that time of day. In the preferred embodiment, each different drug has a distinguishable icon, and the screen "echoes"back the patient's selections by displaying the icon of the selected medication on the timeline chart above the selected time. Thus, if two doses of a particular medication are taken at a particular time, two of the icons corresponding to that medication are displayed above that time on the timeline. Once all of the medications and times have been entered by the patient, touching the "next" region 226 of the screen causes the medication/time information, and a current timestamp to be stored, and the program advances to the next screen.

Figure 19A:
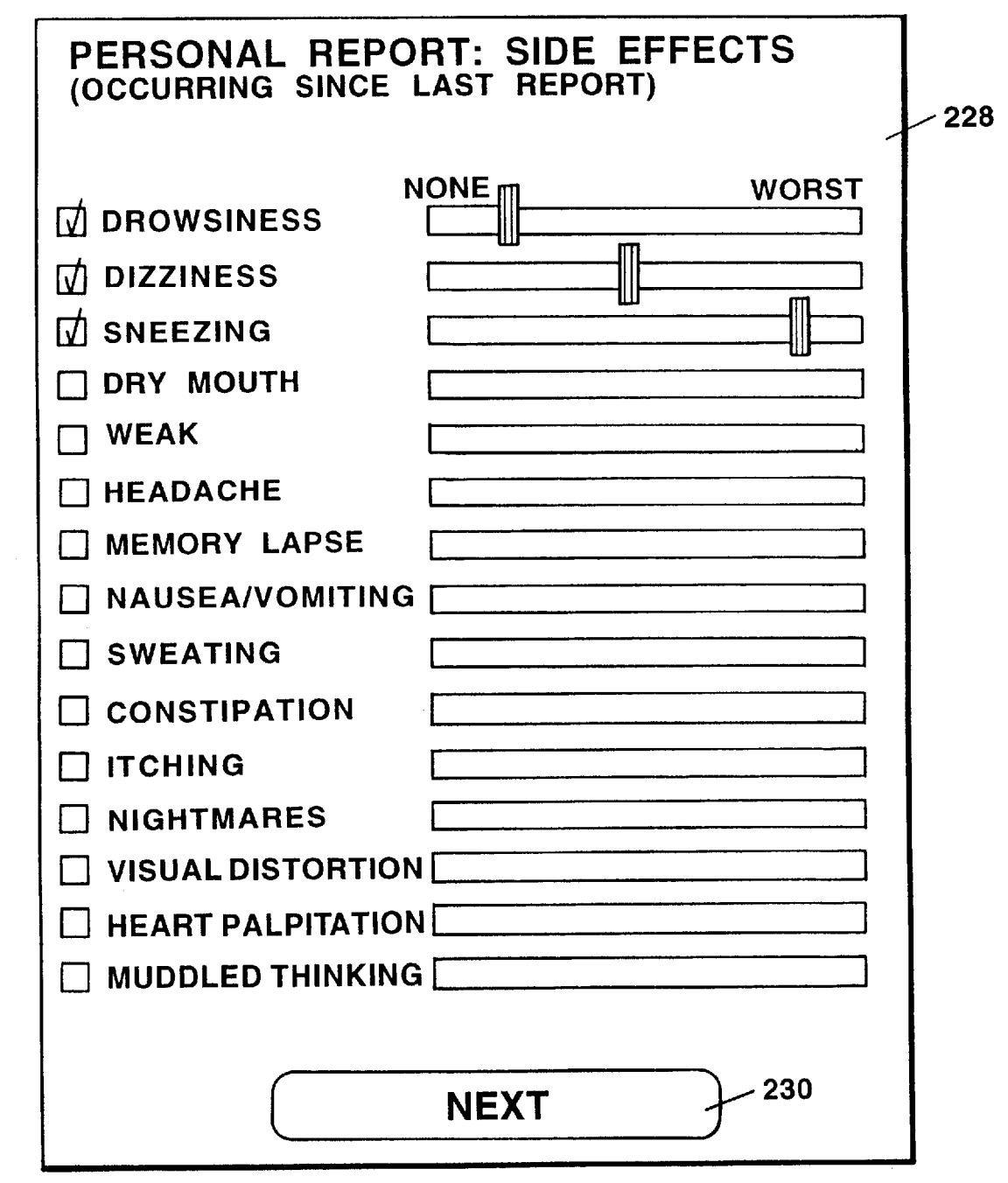

In the preferred embodiment, the medication timeline screen of FIG. 19 is followed by the "side effect" screen 228 shown in FIG. 19A. The side effect screen is a list of typically-encountered side effects, and asks the patient to record those side effects which have been experienced since a last entry was made using the data logger 106 (the list of FIG. 19A is the preferred embodiment, and other side effects may be additionally or alternatively listed). Adjacent to each of the listed side effects is a "check-off" box which may be selected using the pen 202 to indicate that the particular side effect is one which the patient experienced. A sliding scale is also provided adjacent to each listed side effect to allow the patient to select the relative severity of each particular side effect. After the appropriate side effect information has been selected, the patient selects the "next" region 230. This causes the side effect data, along with the current timestamp, to be recorded, and the program advances to the next input screen.

The subjective data logger stores all of the subjective information collected in a local memory unit for later uploading to the database 102 (FIG. 1). The data collected by the data logger is recorded in any well-known format, the specifics of which are not discussed herein. Periodically (preferably once a day) the patient connects the data logger 106 to modem 110 or another data transfer device which transfers the data to the database 102 using a known data transfer protocol. This data, along with the data from the multiparametric monitor, is thereafter available to a physician or scientist with access to the database who may review the information embodied in the data.

Figure 20A:
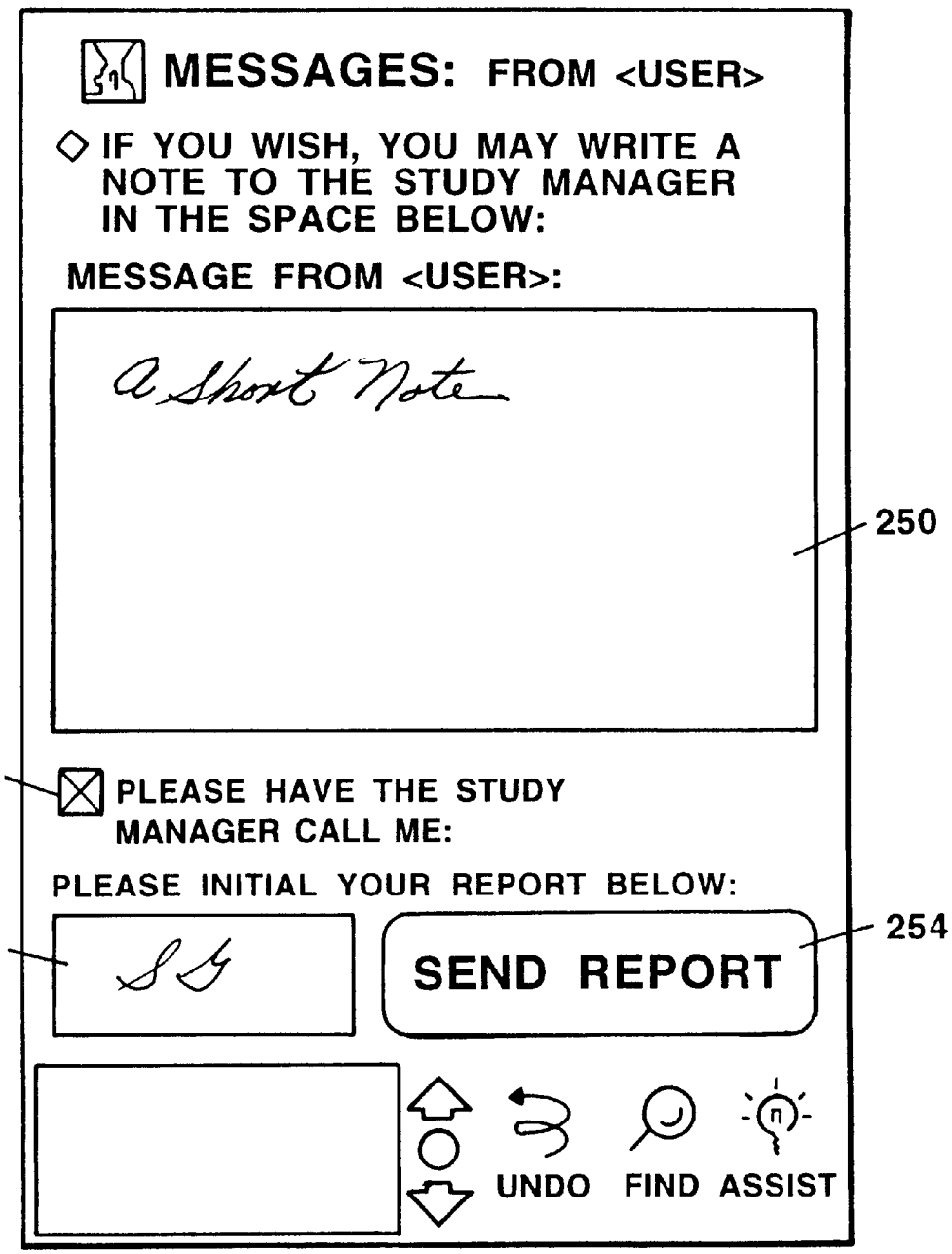
FIG. 20A depicts a message screen upon which a user may enter a message to be received by a party monitoring the database.

In addition to the collection of subjective data, the data logger 106 may be used by the patient to communicate with a physician or researcher who reviews the patient's records in the database. Shown in FIG. 20A is a message screen of the subjective data logger in which a space 250 is provided where the patient may write a message to a person who reviews his or her database records, such as a reviewing physician. In the preferred embodiment, the message is transmitted as bit-mapped data, such that the when displayed by the recipient, it appears in the handwriting of the patient. Although software is available which could be used to convert the message into characters, the handwriting itself may be of use to a reviewing physician in assessing the patient's medical condition and in establishing authenticity of the record.

A messaging screen such as that of FIG. 20A can be used as the last screen of an data input program, so that the patient may comment on any of the previous inputs, as well as anything else of interest. By pressing on the "send report" zone 254 of the screen with the pen 202 (FIG. 15), the entire report, including the message, is transmitted to the database. As shown, the FIG. 20A embodiment also includes a check-off box 256 by which the patient can indicate that he or she wishes a database manager to phone them. The check-off box may be "checked" by touching it with the pen 202.

The preferred embodiment also includes a signature space 252 in which the patient can place his or her signature or initials. Like the message space 250, the signature space is preferably transmitted in a bit-mapped format, allowing the handwriting to be assessed by the reviewing physician, and also allowing the comparison of the signature or initials to a record of the patient's signature or initials. This comparison assists in confirming the patients identity, and may be used as a security measure to help prevent unauthorized access to the patient's database records and to confirm the validity of the uploaded data.

In addition to allowing for messages from the patient to a database manager or reviewing physician, the present invention also provides for the transmission of messages in the other direction. That is, a database manager or reviewing physician can send messages to the patient via the subjective data logger 106. When the data logger 106 is first placed in communication with the database 102 via modem, the data recorded by the patient is uploaded to the database. In addition, any new information to be transmitted to the data logger is downloaded from the database. This information may include modifications to the data logger program or messages to the patient.

Figure 20B:
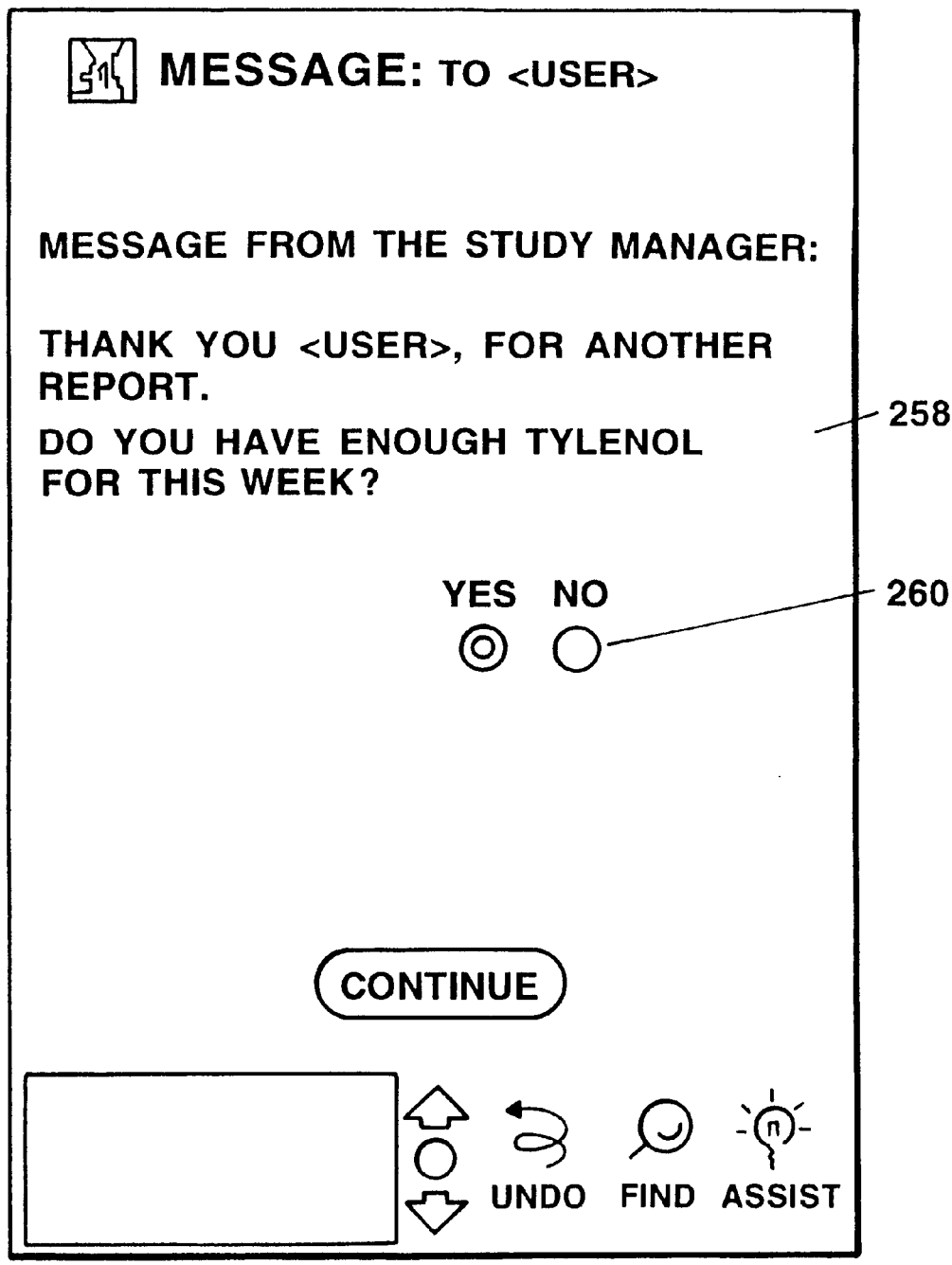
FIG. 20B depicts a message screen upon which a user receives messages and interactive questions from a party monitoring the database.

The message screen of the present invention on which messages are viewed by the patient is showed in FIG. 20B. The messages are printed out in a message region 258 of the screen. As shown, because of the input capabilities of the data logger screen, the messages shown on the screen may include questions with a region provided for a response. In FIG. 20B, a question with a "yes" or "no" response field 260 is provided in which a patient may check off their response to the question. In the preferred embodiment, the "received message" screen would precede the "transmitted message" screen in the sequence of screens presented to the patient. As such, the patient's answers to any questions embedded in the received message can be included with the transmission to the database. Furthermore, messages from the patient can include references to the message received.

In one embodiment of the invention, the communication between the patient and other user's of the patient's database data (such as different doctors consulted by the patient, or the database manager) is structured using a standard electronic mail (E-mail) type protocol. In fact, the system could make use of existing E-mail software. While the database 102 serves as a central location for the storage of all of the patient's data, different destinations for the data could be specified by the patient so that a particular report or message is sent to particular doctors, or other involved parties. Patients using the database may also be divided into groups having particular commonalities. For example, all of the patients of a particular physician might have a particular group designation, thus allowing a single message from the physician to be addressed to all of them.

In general, the present invention may make use of any existing communications protocol which facilitates the data collection, storage and retrieval process. Those skilled in the art will recognize variations in the data communications and storage protocols which may be advantageous to the invention. All of these equivalents are intended to be within the scope of the invention.

Figure 21:
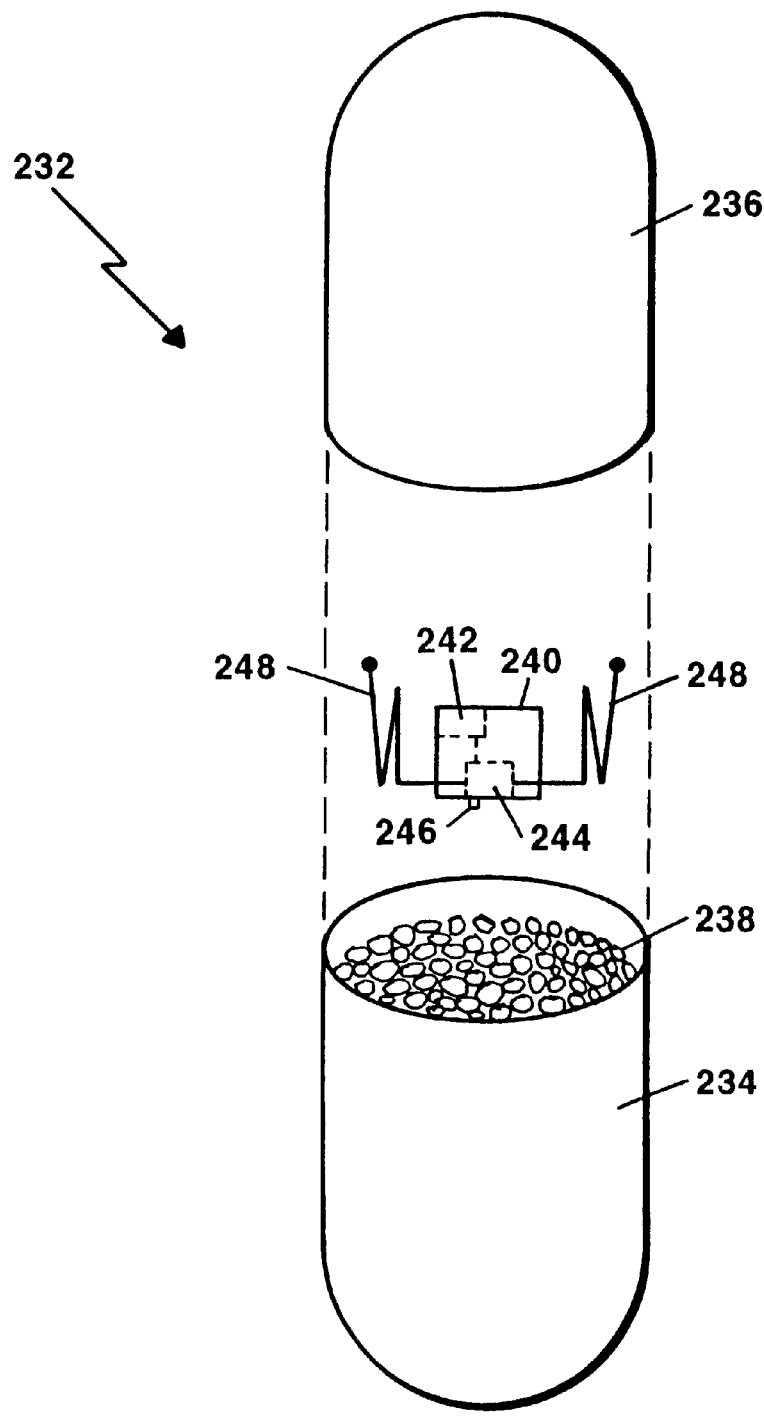
FIG. 21 is an exploded view of an "electronic pill" used with an alternative embodiment of the multiparametric monitor of the present invention.

In one alternative embodiment of the invention, which makes use of the multiparametric monitor, the medication taken by a patient is tracked using an "electronic pill." FIG. 21 is an exploded view of a capsule 232 used in this embodiment which has a first section 234 and a second section 236 which mates with the first section to enclose the contents. This capsule contains the prescribed dosage of medication 238 for the patient, along with a tiny transmitter 240. The transmitter includes a miniature power source 242, and a pulse generating microcircuit 244, which receives power from the power source 242.

In order to conserve power, the microcircuit 244 is inactive while it remains in the capsule. However, once the capsule is dissolved, a liquid sensor 246, of known design, provides a signal to the microcircuit which activates it. The microcircuit 244 then begins outputting the pulsed signal on collapsible leads 248. Also as a result of the capsule dissolving, the leads 248 unfold into a dipole arrangement, and the pulsed signal is conducted from the leads 248 through the patient's body.

The pulsed signal output on the leads 248 is detected at the skin surface by EKG electrodes 140, or other, more advantageously placed detection contacts. The pulsed signal which is generated by the microcircuit is an identification (ID) signal that identifies the medication in the capsule. That is, each different type of medication has its own ID signal which is unique. The signal detected by the electrodes 140 is sampled by ADC 146 and processed by the RT controller 148 as part of its data collection program. This method of detecting the medication taken by the patient is a substitute or supplement for questioning the patient regarding medication using the subjective data logger 106, and is more reliable since it is not limited by the patient's memory or truthfulness. It can therefore be used to validate and cross check the patient's log of drug consumption. The microcircuit is non-toxic and, because of its small size, it eventually is excreted from the body without discomfort to the patient.

While the invention has been shown and described with reference to a preferred embodiment thereof, it will be understood by those skilled in the art that various changes in form and detail may be made therein without departing from the spirit and scope of the invention as defined by the appended claims.

What is claimed is:

1. An in vivo monitoring system comprising:
   an ingestible capsule containing a material to be consumed by a subject;
   a signal generator located within the capsule which outputs a signal having a predetermined signal characteristic, said material being liberated by dissolution of the capsule in the body of the subject; and
   a signal detector at least a portion of which is external to the subject's body, and which detects the signal transmitted from the signal generator.

2. A monitoring system according to claim 1 further comprising a memory storage device in communication with the signal detector and in which a representation of the detected signal is stored.

3. A monitoring system according to claim 1 further comprising an energy storage device in the capsule such that, upon dissolution of the capsule, a transfer of power occurs from the energy storage device to the signal generator.

4. A monitoring system according to claim 1 wherein said signal generator comprises a plurality of electrodes which, when free of the capsule, extend away from one another in a dipole configuration.

5. A monitoring system according to claim 1 wherein said material is a medication.

6. A monitoring system according to claim 1 wherein the dissolution of the capsule occurs in a stomach of the subject.

7. A monitoring system according to claim 1 wherein the signal detector is in contact with a portion of skin of the subject.

8. A monitoring system according to claim 1 wherein the signal is transmitted through tissue of the subject.

9. A monitoring system according to claim 8 wherein the signal is an electrical signal.

10. A medication consumption monitoring system comprising:

an ingestible capsule containing a medication to be consumed by a subject;

a signal generator located within the capsule which outputs an electrical signal having a predetermined characteristic indicative of said medication, said capsule and said medication being liberated by dissolution of the capsule in the stomach acid of a subject; and a signal detector having an input in electrical contact with a portion of the subject's skin and which detects the electrical signal transmitted through tissue of the subject by the signal generator.

11. A medication consumption monitoring system according to claim 1 further comprising a memory storage device in communication with the signal detector and in which a representation of said medication is stored.

12. A medication consumption monitoring system according to claim 1 further comprising an energy storage element device such that, upon dissolution of the capsule, a transfer of power occurs from the energy storage device to the signal generator.

13. A medication consumption monitoring system according to claim 1 wherein said signal generator comprises a plurality of electrodes which, when free of the capsule, extend away from one another in a dipole configuration.

14. A method of monitoring, in vivo, a material consumed by a subject, the method comprising:

initiating the ingestion of an ingestible capsule by the subject that contains the material to be consumed, the capsule additionally containing a signal generator that outputs a signal having a predetermined signal characteristic, said material and signal generator being liberated by dissolution of the capsule in the body of the subject; and detecting the signal transmitted by the signal generator with a signal detector, at least a portion of which is external to the subject's body.

15. A method according to claim 14 further comprising storing a representation of the detected signal in a memory storage device that is in communication with the signal detector.

16. A method according to claim 14 wherein the signal generator is powered by an energy storage device located in the capsule that transfers power to the signal generator upon dissolution of the capsule.

17. A method according to claim 14 wherein said signal generator comprises a plurality of electrodes which, when free of the capsule, extend away from one another in a dipole configuration.

18. A method according to claim 14 wherein said material is a medication.

19. A method according to claim 14 wherein the dissolution of the capsule occurs in a stomach of the subject.

20. A method according to claim 14 wherein the signal detector is in contact with a portion of skin of the subject.

21. A method according to claim 14 wherein the signal is transmitted through tissue of the subject.

22. A method according to claim 14 wherein the signal is an electrical signal.

23. A method of monitoring, in vivo, a medication consumed by a subject, the method comprising:

initiating the ingestion of an ingestible capsule by the subject that contains the medication to be consumed, the capsule additionally containing a signal generator that outputs an electrical signal having a predetermined signal characteristic indicative of the medication, said medication and signal generator being liberated by dissolution of the capsule in the body of the subject; and detecting the signal transmitted by the signal generator with a signal detector in contact with a portion of the subject's skin, the detector detecting the electrical signal transmitted through tissue of the subject by the signal generator.

24. A method according to claim 23 further comprising storing a representation of the medication in a memory storage device in communication with the signal detector.

25. A method according to claim 23 wherein power is provided to the signal generator from an energy storage element in the capsule that transfers the power upon dissolution of the capsule.

26. A method according to claim 23 wherein said signal generator comprises a plurality of electrodes which, when free of the capsule, extend away from one another in a dipole configuration.

* * * * *